United States Patent [19]

Fischer et al.

[11] Patent Number: 5,602,078
[45] Date of Patent: Feb. 11, 1997

[54] DIALKYL-1-H-3-(2,4-DIMETHYLPHENYL)-PYRROLIDINE-2,4-DIONES, THEIR PREPARATION AND THEIR USE

[75] Inventors: Reiner Fischer, Monheim; Thomas Bretschneider, Siegburg; Bernd-Wieland Krüger, Bergisch Gladbach; Hans-Joachim Santel, Leverkusen; Markus Dollinger; Christoph Erdelen, both of Leichlingen; Ulrike Wachendorff-Neumann, Monheim, all of Germany

[73] Assignee: Bayer Aktiengesellschaft, Leverkusen, Germany

[21] Appl. No.: 566,781

[22] Filed: Dec. 4, 1995

Related U.S. Application Data

[62] Division of Ser. No. 200,138, Feb. 22, 1994, Pat. No. 5,504,057.

[30] Foreign Application Priority Data

Mar. 1, 1993 [DE] Germany .............. 43 06 259.8

[51] Int. Cl.⁶ .............. A01N 43/36; C07D 207/12
[52] U.S. Cl. .............. 504/283; 548/408; 548/544
[58] Field of Search .............. 548/408, 544; 504/283

[56] References Cited

FOREIGN PATENT DOCUMENTS

| 415185 | 3/1991 | European Pat. Off. . |
| 0456063 | 11/1991 | European Pat. Off. . |
| 0521334 | 1/1993 | European Pat. Off. . |
| 0595130 | 5/1994 | European Pat. Off. . |
| 0596298 | 5/1994 | European Pat. Off. . |

OTHER PUBLICATIONS

CA 116:106083h, Preparation . . . insecticides, Krausdopf et al., p. 754, 1992.
CA 119:8676w: Substituted . . . derivatives, Fischer, et al., p. 89±, 1993.

Primary Examiner—Joseph K. McKane
Attorney, Agent, or Firm—Sprung Horn Kramer & Woods

[57] ABSTRACT

Dialkyl-1-H-3-(2,4-dimethylphenyl)-pyrrolidine-2,4-diones of the formula (I)

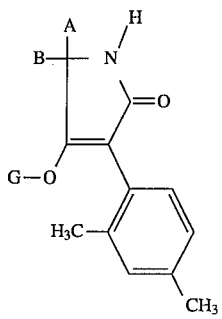

in which
  A represents alkyl which is optionally substituted by halogen and
  B represents $C_2$–$C_{10}$-alkyl or
  A and B together with the carbon atom to which they are bonded represent an unsubstituted cycle,
  G represents hydrogen,
  L and M represent oxygen and/or sulphur. These compounds possess herbicidal and pesticidal activity.

7 Claims, No Drawings

DIALKYL-1-H-3-(2,4-DIMETHYLPHENYL)-PYRROLIDINE-2,4-DIONES, THEIR PREPARATION AND THEIR USE

This application is a divisional, of application Ser. No. 08/200,138, filed Feb. 22, 1994 now U.S. Pat. No. 5,504,057.

The invention relates to novel dialkyl-1-H-3-(2,4-dimethylphenyl)-pyrrolidine-2,4-diones, to processes for their preparation and to their use as pesticides (in particular as insecticides and acaricides) and as herbicides.

3-Acyl-pyrrolidine-2,4-diones have previously been described as having pharmaceutical properties (S. Suzuki et al. Chem. Pharm. Bull. 15 1120 (1967)). Furthermore, N-phenyl-pyrrolidine-2,4-diones were synthesized by R. Schmierer and H. Mildenberger (Liebigs Ann. Chem. 1985 1095). A biological activity of these compounds has not been described.

EP-A 0,262,399 discloses compounds of a similar structure (3-aryl-pyrrolidine-2,4-diones), from which, however, no herbicidal, insecticidal or acaricidal activity has been disclosed. Unsubstituted, bicyclic 3-aryl-pyrrolidine-2,4-dione derivatives (EP-A 355,599 and EP 415,211), substituted bicyclic 3-aryl-pyrrolidine-2,4-dione derivatives (EP 501,129) and substituted mono-cyclic 3-aryl-pyrrolidine-2,4-dione derivatives (EP-A 377,893, EP 442,077 and EP 497,127) are known and have a herbicidal, insecticidal or acaricidal activity.

Also known are polycyclic 3-arylpyrrolidine-2,4-dione derivatives (EP 442,073) and 1-H-3-arylpyrrolidine-dione derivatives (EP 456,063 and EP 521,334).

Novel dialkyl-1-H-3-(2,4-dimethylphenyl)-pyrrolidine-2,4-diones of the formula (I)

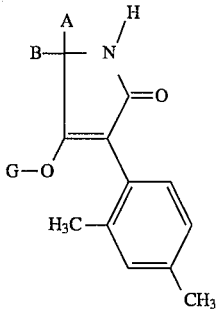

(I)

have now been found,
in which
A represents alkyl which is optionally substituted by halogen and
B represents $C_2$–$C_{10}$-alkyl or
A and B together with the carbon atom to which they are bonded represent an unsubstituted cycle,
G represents hydrogen (a) or the groups

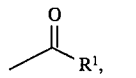  (b)

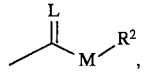  (c)

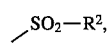  (d)

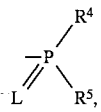  (e)

E  (f)

or

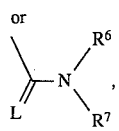  (g)

E represents a metal ion equivalent or an ammonium ion,

L and M represents oxygen and/or sulphur, $R^1$ represents in each case optionally halogen-substituted alkyl, alkenyl, alkoxyalkyl, alkyl-thioalkyl, poly-alkoxyalkyl or cycloalkyl, it being possible for the latter to be interrupted by hetero atoms, or represents optionally substituted phenyl, optionally substituted phenylalkyl, substituted hetaryl, substituted phenoxyalkyl or substituted hetaryloxyalkyl, $R^2$ represents in each case optionally halogen-substituted alkyl, alkenyl, alkoxyalkyl, polyalkoxyalkyl or in each case optionally substituted cycloalkyl, phenyl or benzyl, $R^3$, $R^4$ and $R^5$ independently of one another represent in each case optionally halogen-substituted alkyl, alkoxy, cycloalkyloxy, alkylamino, dialkylamino, alkylthio, alkenylthio or cycloalkylthio and in each case optionally substituted phenyl, phenoxy, benzyloxy or phenylthio, $R^6$ and $R^7$ independently of one another represent hydrogen, in each case optionally halogen-substituted alkyl, alkenyl, alkoxy or alkoxy-alkyl, optionally substituted phenyl, optionally substituted benzyl, or together with the N-atom to which they are bound represent a cycle which is optionally interrupted by oxygen or sulphur.

Taking into consideration the various meanings (a), (b), (c), (d), (e), (f) and (g) of group G in the general formula (I), the following main structures (Ia) to (Ig) result:

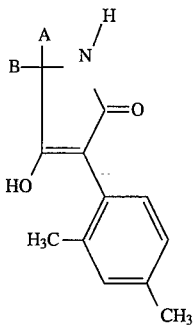

(Ia)

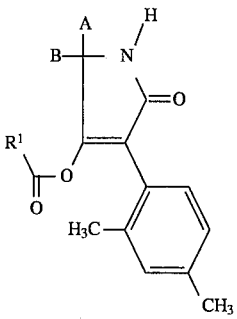

(Ib)

-continued

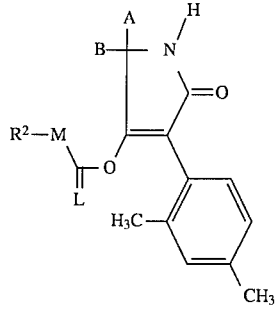 (Ic)

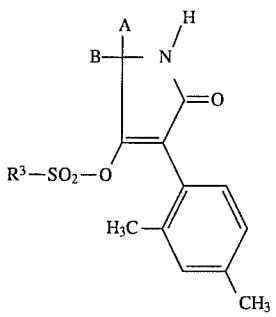 (Id)

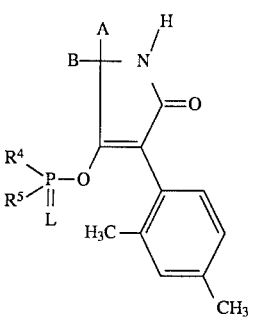 (Ie)

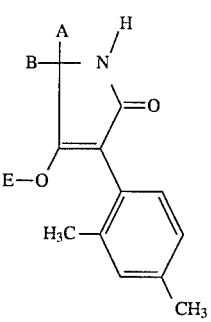 (If)

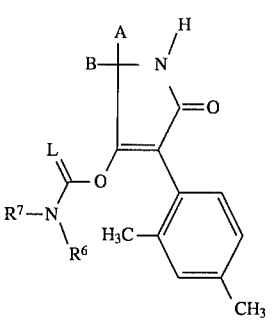 (Ig)

in which

A, B, E, L, M, $R^1$, $R^2$, $R^3$, $R^4$, $R^5$, $R^6$ and $R^7$ have the abovementioned meanings.

Due to one or more centres of chirality, the compounds of the formula (Ia)–(Ig) are generally obtained as a mixture of stereoisomers which, if appropriate, can be separated in the customary manner. They can be used in the form of their diastereomer mixture and also as pure diastereomers or enantiomers. The following text will always mention compounds of the formula (Ia) to (Ig), for simplicity's sake, even though this is to be understood as meaning the pure compounds and also the mixtures containing various proportions of isomeric, enantiomeric and stereomeric compounds.

Furthermore, it has been found that the novel dialkyl-1-H-3-(2,4-dimethylphenyl)-pyrrolidine-2,4-diones of the formula (I) are obtained by one of the processes described below.

(A) Dialkyl-1-H-3-(2,4-dimethylphenyl)-pyrrolidine-2,4-diones or their enols of the formula (Ia)

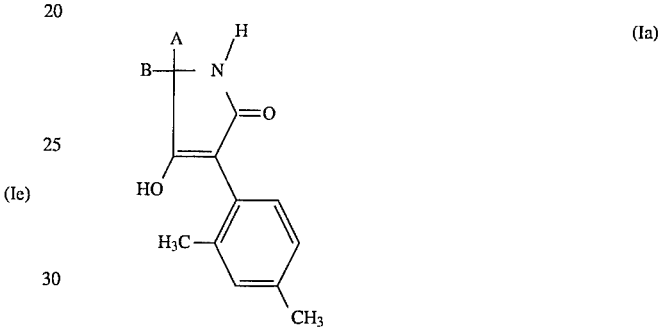 (Ia)

in which

A and B have the abovementioned meaning, are obtained when N-acylamino acid esters of the formula (II)

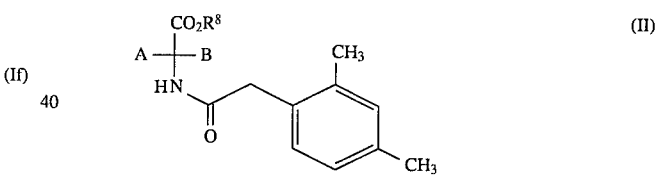 (II)

in which

A and B have the abovementioned meaning and $R^8$ represents alkyl, are subjected to an intramolecular condensation reaction in the presence of a diluent and in the presence of a base; or (B) compounds of the formula (Ib)

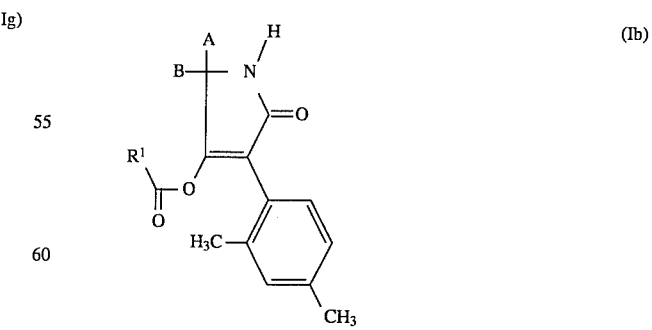 (Ib)

in which

A, B and $R^1$ have the abovementioned meaning, are obtained when compounds of the formula (Ia)

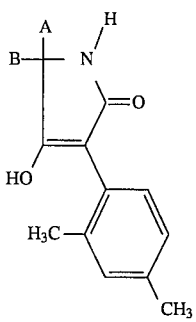

(Ia)

in which

A and B have the abovementioned meaning,
are reacted

α) with acid halides of the general formula (III)

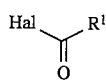  (III)

in which

R$^1$ has the abovementioned meaning and

Hal represents halogen, in particular chlorine and bromine, if appropriate in the presence of a diluent and if appropriate in the presence of an acid-binding agent, or β) with carboxylic anhydrides of the general formula (IV)

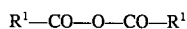

$R^1$—CO—O—CO—$R^1$ (IV)

in which

R$^1$ has the abovementioned meaning, if appropriate in the presence of a diluent and if appropriate in the presence of an acid-binding agent;

or (C) compounds of the formula (Ic-1)

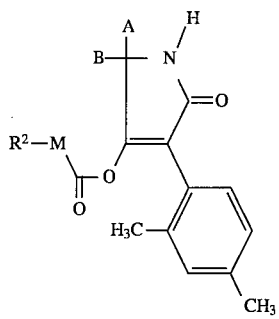

(Ic-1)

in which

A, B and R$^2$ have the abovementioned meaning, and

M represents oxygen or sulphur, are obtained when compounds of the formula (Ia)

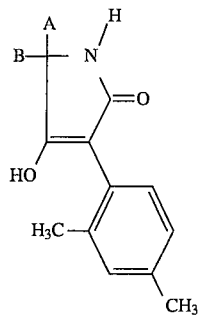

(Ia)

in which

A and B have the abovementioned meaning,
are reacted with chloroformic ester or chloroformic thioester of the general formula (V)

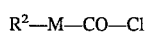

R$^2$—M—CO—Cl (V)

in which

R$^2$ and M have the abovementioned meaning, if appropriate in the presence of a diluent and if appropriate in the presence of an acid-binding agent; or (D) compounds of the formula (Ic-2)

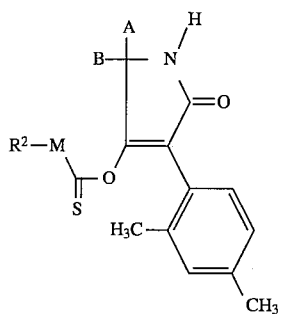

(Ic-2)

in which

A, B and R$^2$ have the abovementioned meaning and

M represents oxygen or sulphur, are obtained when compounds of the formula (Ia)

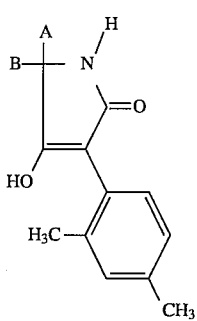

(I-a)

in which

A and B have the abovementioned meaning, are reacted

α) with chloromonothioformic esters or chlorodithioformic esters of the general formula (VI)

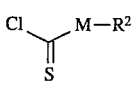  (VI)

in which

M and $R^2$ have the abovementioned meaning, if appropriate in the presence of a diluent and if appropriate in the presence of an acid-binding agent, or β) with carbon disulphide and subsequently with alkyl halides of the general formula (VII)

$R^2$—Hal     (VII)

in which $R^2$ has the abovementioned meaning and

Hal represents chlorine, bromine or iodine, if appropriate in the presence of a diluent; or (E) compounds of the formula (Id)

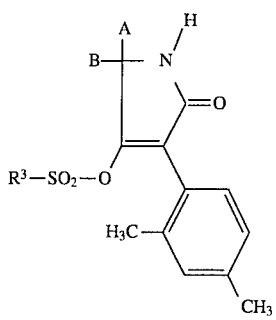
(Id)

in which

A, B and $R^3$ have the abovementioned meaning, are obtained when compounds of the formula (Ia)

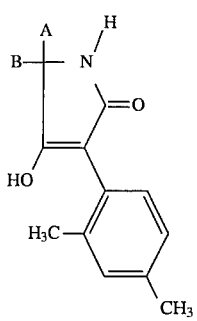
(Ia)

in which

A and B have the abovementioned meaning, are reacted with sulphonyl chlorides of the general formula (VIII)

$R^3$—$SO_2$—Cl     (VIII)

in which $R^3$ has the abovementioned meaning, if appropriate in the presence of a diluent and if appropriate in the presence of an acid-binding agent; or (F) compounds of the formula (Ie)

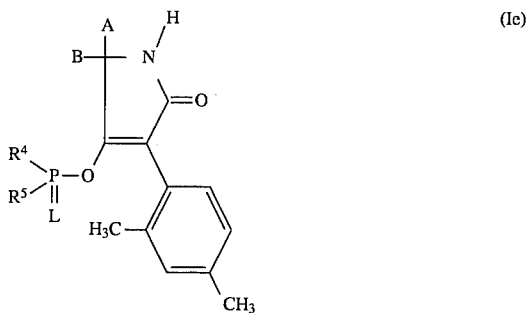
(Ie)

in which

A, B, L, $R^4$ and $R^5$ have the abovementioned meaning, are obtained when 1-H-3-(2,4-dimethylphenyl)-pyrrolidine-2,4-diones of the formula (Ia) or their enols

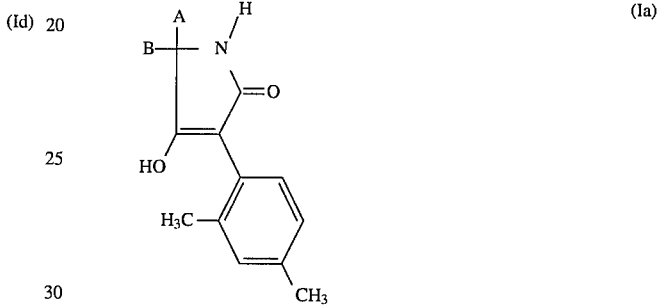
(Ia)

in which

A and B have the abovementioned meaning, are reacted with phosphorus compounds of the general formula (IX)

(IX)

in which

L, $R^4$ and $R^5$ have the abovementioned meaning and

Hal represents halogen, in particular chlorine and bromine, if appropriate in the presence of a diluent and if appropriate in the presence of an acid-binding agent; or (G) compounds of the formula (If)

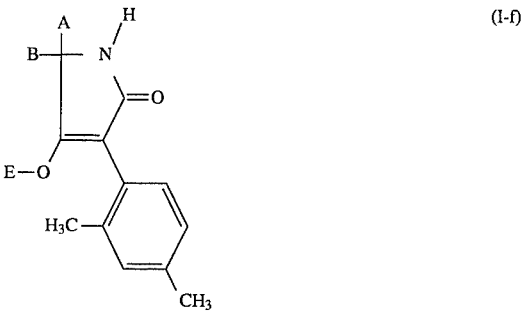
(I-f)

in which

A and B have the abovementioned meaning and

E represents a metal ion equivalent or an ammonium ion, are obtained when compounds of the formula (Ia)

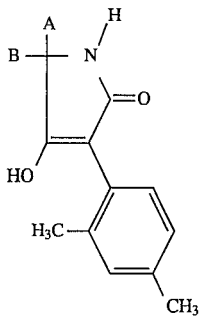

in which

A and B have the abovementioned meaning,
are reacted with metal hydroxides or amines of the general formulae (X) and (XI)

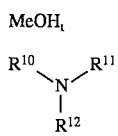

in which

Me represents mono- or divalent metal ions, t represent the number 1 or 2 and $R^{10}$, $R^{11}$ and $R^{12}$ independently of one another represent hydrogen or alkyl, if appropriate in the presence of a diluent.

(H) Furthermore, it has been found that compounds of the formula (I)

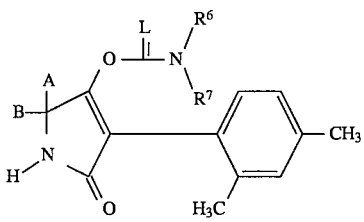

in which

A, B, L, $R^6$ and $R^7$ have the abovementioned meaning, are obtained when compounds of the formula (Ia)

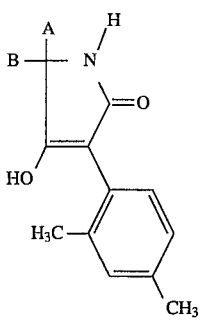

in which

A and B have the abovementioned meaning,
are reacted

α) with compounds of the general formula (XII)

in which

L and $R^6$ have the abovementioned meaning, if appropriate in the presence of a diluent and if appropriate in the presence of a catalyst, or β) with carbamoyl chlorides or thiocarbamoyl chlorides of the general formula (XIII)

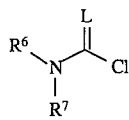

in which

L, $R^6$ and $R^7$ have the abovementioned meaning, if appropriate in the presence of a diluent and if appropriate in the presence of an acid-binding agent.

Furthermore, it has been found that the novel dialkyl-1-H-3-(2,4-dimethylphenyl)-pyrrolidine-2,4-diones of the formula (I) are distinguished by outstanding insecticidal, acaricidal and herbicidal activities.

The following applies to the general formulae of the present application:

A can preferably represent straight-chain or branched $C_1$–$C_{10}$-alkyl which is optionally substituted by halogen, B can preferably represent straight-chain or branched $C_2$–$C_{10}$-alkyl, or A, B and the carbon atom to which they are bonded can preferably represent an unsubstituted $C_3$–$C_{12}$-spiro cycle, A particularly preferably represents straight-chain or branched $C_1$–$C_8$-alkyl which is optionally substituted by fluorine and/or chlorine, B particularly preferably represents straight-chain or branched $C_2$–$C_8$-alkyl or A, B and the carbon atom to which they are bonded particularly preferably represent an unsubstituted $C_3$–$C_8$-spiro cycle, A very particularly preferably represents straight-chain or branched $C_1$–$C_6$-alkyl which is optionally substituted by fluorine, B very particularly preferably represents straight-chain or branched $C_2$–$C_4$-alkyl or A, B and the carbon atom to which they are bonded very particularly preferably represent an unsubstituted $C_3$–$C_7$-spiro cycle, G preferably represents hydrogen (a) or the groups

 (b)

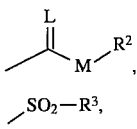 (c)

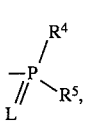 (d)

 (e)

E (f)

or

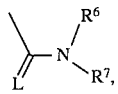

in which

E represents a metal ion equivalent or an ammonium ion and

L and M in each case represent oxygen and/or sulphur, $R^1$ represents in each case optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, $C_1$–$C_8$-polyalkoxy-$C_1$–$C_8$-alkyl or cycloalkyl having 3 to 8 ring atoms, it being possible for the latter to be interrupted by oxygen and/or sulphur atoms, or represents phenyl which is optionally substituted by halogen, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$-alkylsulphonyl, or represents phenyl-$C_1$–$C_6$-alkyl which is optionally substituted by halogen, $C_1$–$C_6$-alkyl, $C_1$–$C_6$-alkoxy, $C_1$–$C_6$-halogenoalkyl or $C_1$–$C_6$-halogenoalkoxy, or represents hetaryl which is optionally substituted by halogen and/or $C_1$–$C_6$-alkyl, or represents phenoxy-$C_1$–$C_6$-alkyl which is optionally substituted by halogen and/or $C_1$–$C_6$-alkyl, or represents hetaryloxy-$C_1$–$C_6$-alkyl which is optionally substituted by halogen, amino and/or $C_1$–$C_6$-alkyl, $R^2$ represents $C_1$–$C_{20}$-alkyl, $C_3$–$C_{20}$-alkenyl, $C_1$–$C_8$-alkoxy-$C_2$–$C_8$-alkyl or $C_1$–$C_8$-polyalkoxy-$C_2$–$C_8$-alkyl, each of which is optionally substituted by halogen, or represents cycloalkyl, phenyl or benzyl, each of which is optionally substituted by halogen, nitro, $C_1$–$C_6$-alkyl, $C_1$–$C_6$-alkoxy or $C_1$–$C_6$-halogenoalkyl, $R^3$, $R^4$ and $R^5$ independently of one another represent $C_1$–$C_8$-alkyl, $C_1$–$C_8$-alkoxy, $C_3$–$C_7$-cycloalkyloxy, $C_1$–$C_8$-alkylamino, di-($C_1$–$C_8$)-alkylamino, $C_1$–$C_8$-alkylthio, $C_3$–$C_8$-alkenylthio or $C_3$–$C_7$-cycloalkylthio, each of which is optionally substituted by halogen, or represent phenyl, phenoxy, benzyloxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl, $R^6$ and $R^7$ independently of one another represent hydrogen or represent $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl, each of which is optionally substituted by halogen, or represent phenyl which is optionally substituted by halogen, $C_1$–$C_8$-halogenoalkyl, $C_1$–$C_8$-alkyl or $C_1$–$C_8$-alkoxy, or represent benzyl which is optionally substituted by halogen, $C_1$–$C_8$-alkyl, $C_1$–$C_8$-halogenoalkyl or $C_1$–$C_8$-alkoxy, or together with the N-atom to which they are bound represent a ring having 3–6 C-atoms which is optionally interrupted by oxygen or sulphur, G particularly preferably represents hydrogen (a) or the groups

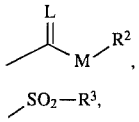

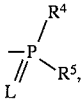

E (f)

or

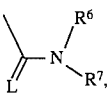

in which

E represents a metal ion equivalent or an ammonium ion,

L and M in each case represent oxygen and/or sulphur, $R^1$ represents in each case optionally halogen-substituted $C_1$–$C_{16}$-alkyl, $C_2$–$C_{16}$-alkenyl, $C_1$–$C_6$-alkoxy-$C_1$–$C_6$-alkyl, $C_1$–$C_{16}$-alkylthio-$C_1$–$C_6$-alkyl, $C_1$–$C_6$-polyalkoxy-$C_1$–$C_6$-alkyl or cycloalkyl having 3 to 7 ring atoms which can be interrupted by 1–2 oxygen and/or sulphur atoms, or represents phenyl which is optionally substituted by halogen, nitro, $C_1$–$C_4$-alkyl, $C_1$–$C_4$-alkoxy, $C_1$–$C_3$-halogenoalkyl, $C_1$–$C_3$-halogenoalkoxy, $C_1$–$C_6$-alkylthio or $C_1$–$C_6$-alkylsulphonyl, or represents phenyl-$C_1$–$C_4$-alkyl which is optionally substituted by halogen, $C_1$–$C_4$-alkyl, $C_1$–$C_4$-alkoxy, $C_1$–$C_3$-halogenoalkyl or $C_1$–$C_3$-halogenoalkoxy, or represents hetaryl which is optionally substituted by fluorine, chlorine, bromine- and/or $C_1$–$C_4$-alkyl, or represents phenoxy-$C_1$–$C_5$-alkyl which is optionally substituted by fluorine, chlorine, bromine and/or $C_1$–$C_4$-alkyl, or represents hetaryloxy-$C_1$–$C_5$-alkyl which is optionally substituted by fluorine, chlorine, bromine, amino and/or $C_1$–$C_4$-alkyl, $R^2$ represents $C_1$–$C_{16}$-alkyl, $C_3$–$C_{16}$-alkenyl, $C_1$–$C_6$-alkoxy-$C_2$–$C_6$-alkyl or $C_1$–$C_6$-polyalkoxy-$C_2$–$C_6$-alkyl, each of which is optionally substituted by halogen, or represents cycloalkyl, phenyl or benzyl, each of which is optionally substituted by halogen, nitro, $C_1$–$C_4$-alkyl, $C_1$–$C_3$-alkoxy or $C_1$–$C_3$-halogenoalkyl, $R^3$, $R^4$ and $R^5$ independently of one another represent $C_1$–$C_6$-alkyl, $C_1$–$C_6$-alkoxy, $C_3$–$C_6$-cycloalkyloxy, $C_1$–$C_6$-alkylamino, di-($C_1$–$C_6$)-alkylamino, $C_1$–$C_6$-alkylthio, $C_3$–$C_6$-alkenylthio or $C_3$–$C_6$-cycloalkylthio, each of which is optionally substituted by halogen, or represent phenyl, phenoxy, benzyloxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl, $R^6$ and $R^7$ independently of one another represent hydrogen, $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, each of which is optionally substituted by halogen, or represent phenyl which is optionally substituted by halogen, $C_1$–$C_5$-halogenoalkyl, $C_1$–$C_5$-alkyl or $C_1$–$C_5$-alkoxy, or represent benzyl which is optionally substituted by halogen, $C_1$–$C_5$-alkyl, $C_1$–$C_5$-halogenoalkyl or $C_1$–$C_5$-alkoxy, or together with the N-atom to which they are bound, represent a ring having 3–6 C-atoms which is optionally interrupted by oxygen or sulphur.

G very particularly preferably represents hydrogen (a) or the groups

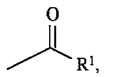 (b)

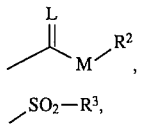 (c)

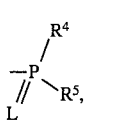 (d)

 (e)

E (f)

or

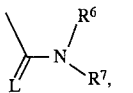 (g)

in which

E represents a metal ion equivalent or an ammonium ion and

L and M represent oxygen and/or sulphur, $R^1$ represents in each case optionally fluorine- or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, $C_1$–$C_4$-polyalkoxy-$C_1$–$C_4$-alkyl or cycloalkyl having 3 to 6 ring atoms which can be interrupted by 1 to 2 oxygen and/or sulphur atoms, or represents phenyl which is optionally substituted by fluorine, chlorine, bromine, methyl, ethyl, propyl, i-propyl, methoxy, ethoxy, trifluoromethyl, trifluoromethoxy, nitro, methylthio, ethylthio., methylsulphonyl or ethylsulphonyl, or represents phenyl-$C_1$–$C_3$-alkyl which is optionally substituted by fluorine, chlorine, bromine, methyl, ethyl, propyl, i-propyl, methoxy, ethoxy, trifluoromethyl or trifluoromethoxy, or represents furanoyl, thienyl, pyridyl, pyrimidyl, thiazolyl and pyrazolyl, each of which is optionally substituted by fluorine, chlorine, bromine, methyl or ethyl, or represents phenoxy-$C_1$–$C_4$-alkyl which is optionally substituted by fluorine, chlorine, methyl or ethyl, or represents pyridyloxy-$C_1$–$C_4$-alkyl, pyrimidyloxy-$C_1$–$C_4$-alkyl and thiazolyloxy-$C_1$–$C_4$-alkyl, each of which is optionally substituted by fluorine, chlorine, amino, methyl or ethyl, $R^2$ represents $C_1$–$C_{14}$-alkyl, $C_3$–$C_{14}$-alkenyl, $C_1$–$C_4$-alkoxy-$C_2$–$C_6$-alkyl or $C_1$–$C_4$-polyalkoxy-$C_2$–$C_6$-alkyl, each of which is optionally substituted by fluorine or chlorine, or represent cycloalkyl, phenyl or benzyl, each of which is optionally substituted by fluorine, chlorine, nitro, methyl, ethyl, propyl, i-propyl, methoxy, ethoxy or trifluoromethyl, $R^3$, $R^4$ and $R^5$ independently of one another represent $C_1$–$C_4$-alkyl, $C_1$–$C_4$-alkoxy, $C_1$–$C_4$-alkylamino, di-($C_1$–$C_4$)-alkylamino or $C_1$–$C_4$-alkylthio, each of which is optionally substituted by fluorine or chlorine, or represent phenyl, phenoxy, benzyloxy or phenylthio, each of which is optionally substituted by fluorine, chlorine, bromine, nitro, cyano, $C_1$–$C_2$-alkoxy, $C_1$–$C_4$-fluoroalkoxy, $C_1$–$C_2$-alkylthio, $C_1$–$C_2$-fluoroalkylthio or $C_1$–$C_3$-alkyl.

$R^6$ and $R^7$ independently of one another represent hydrogen, or represent $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, each of which is optionally substituted by fluorine, chlorine or bromine, or represent phenyl which is optionally substituted by fluorine, chlorine, bromine, $C_1$–$C_4$- halogenoalkyl, $C_1$–$C_4$-alkyl or $C_1$–$C_4$-alkoxy, or represent benzyl which is optionally substituted by fluorine, chlorine, bromine, $C_1$–$C_4$-alkyl, $C_1$–$C_4$-halogenoalkyl or $C_1$–$C_4$-alkoxy, or together with the N-atom to which they are bound represent a ring having 4–6 C-atoms which is optionally interrupted by oxygen or sulphur.

If, according to process (A), ethyl N-2,4-dimethylphenyl-acetyl-2-amino-2-methyl-butyrate is used, the course of the process according to the invention can be represented by the following equation:

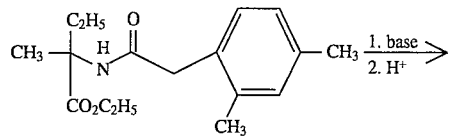

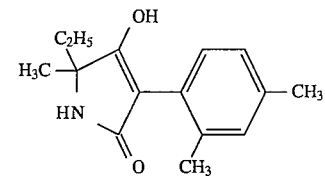

If, according to process (B) (variant α) 3-(2,4-dimethylphenyl)-5-methyl-5-propyl-pyrrolidine-2,4-dione and pivaloyl chloride are used as starting substances, the course of the process according to the invention can be represented by the following equation:

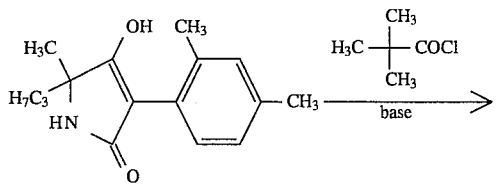

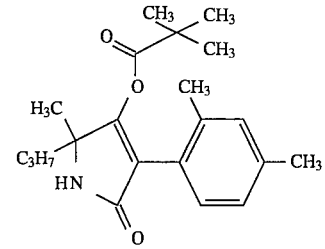

If, according to process B (variant β), 3-(2,4-dimethylphenyl)-5,5-diethyl-pyrrolidine-2,4-dione and acetic anhydride are used as starting compounds, the course of the process according to the invention can be represented by the following equation:

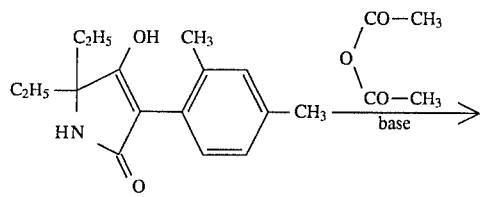

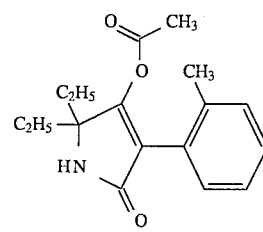

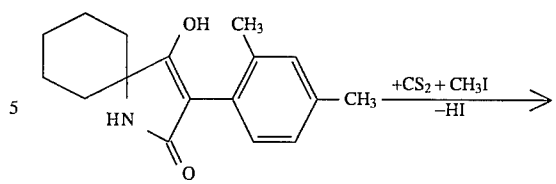

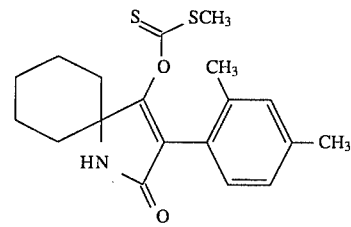

If, according to process (C), 3-(2,4-dimethylphenyl)-5-sec.-butyl-5-methyl-pyrrolidine-2,4-dione and ethoxy-ethyl chloroformate are used as starting compounds, the course of the process according to the invention can be represented by the following equation:

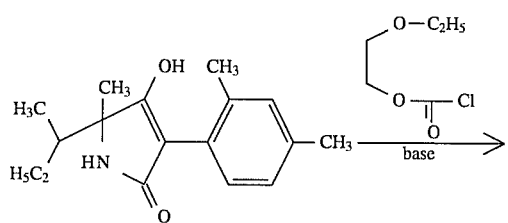

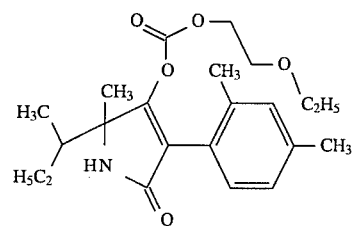

If, according to process ($D_\alpha$), 3-(2,4-dimethylphenyl)-5-isopropyl-5-methyl-pyrrolidine-2,4-dione and methyl chloromonothioformate are used as starting materials, the course of the reaction can be represented as follows:

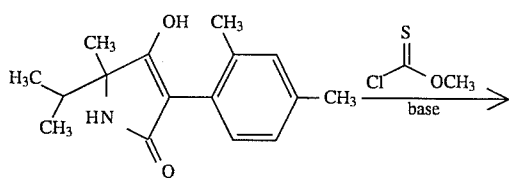

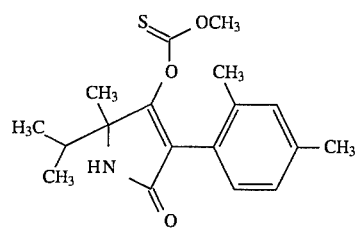

If, according to process ($D_\beta$), 3- (2,4-dimethylphenyl)-5,5-pentamethylenepyrrolidine-2,4-dione, carbon disulphide and methyl iodide are used as starting components, the course of the reaction can be represented as follows:

If, according to process (E) 3- (2,4-dimethylphenyl)-5-isobutyl-5-methyl-pyrrolidine-2,4-dione and methane-sulphonyl chloride are used as the starting material, the course of the reaction can be represented by the following equation:

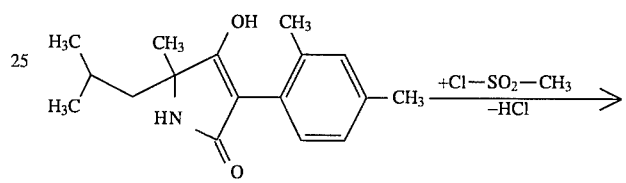

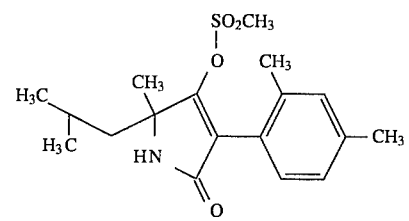

If, according to process (F), 3-(2,4-dimethylphenyl)-5.5-dipropyl-pyrrolidine-2,4-dione and 2,2,2-trifluoroethyl methanethio-chlorophosphonate are used as starting materials, the course of the reaction can be represented by the following equation:

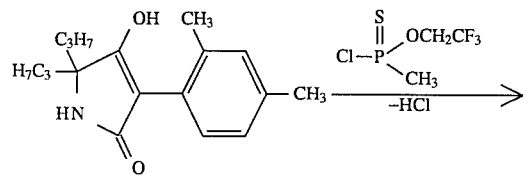

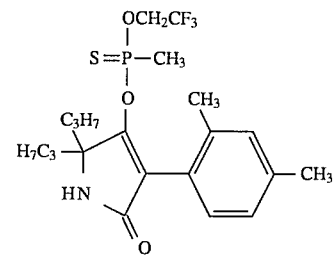

If, according to process (G), 3-(2,4-dimethylphenyl)-5,5-diethyl-pyrrolidine-2,4-dione and NaOH are used as the components, the course of the process according to the invention can be represented by the following equation:

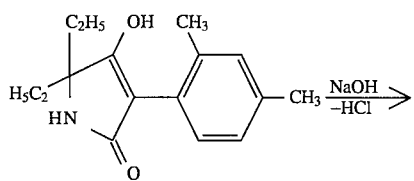

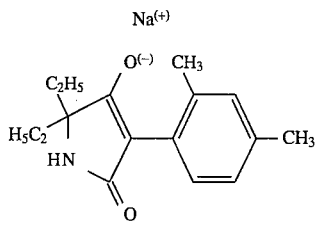

If, according to process (H$_\alpha$), 3-(2,4-dimethylphenyl)-5,5-hexamethylene-pyrrolidine-2,4-dione and ethyl isocyanate are used as starting materials, the course of the reaction can be represented by the following equation:

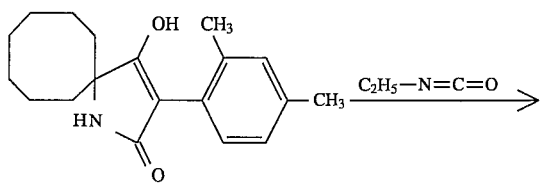

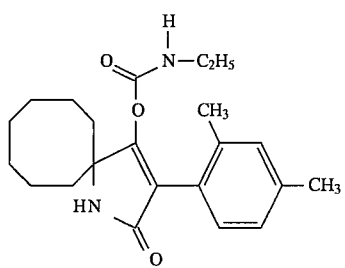

If, according to process (H$_\beta$), 3-(2,4-dimethylphenyl)-5-butyl-5-methyl-pyrrolidine-2,4-dione and dimethylcarbamoyl chloride are used as starting materials, the course of the reaction can be represented by the following equation:

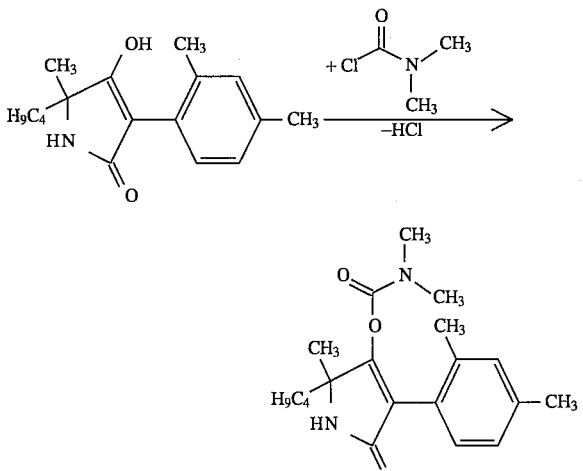

Some of the compounds of the formula (II)

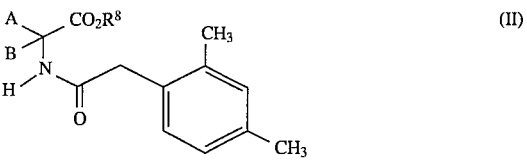

in which

A, B and $R^8$ have the abovementioned meaning, which are required as starting substances in processes (A) according to the invention, are known and the subject-matter of a German Patent Application by the applicant company which has hitherto not been disclosed (P 42 36 400).

Acylamino acid esters of the formula (II) are obtained, for example, when amino acid derivatives of the formula (XIV)

in which

R9' represents hydrogen (XIVa) and alkyl (XIVb) and

A and B have the abovementioned meaning, are acylated with 2,4-dimethylphenylacetyl chloride, of the formula (XV)

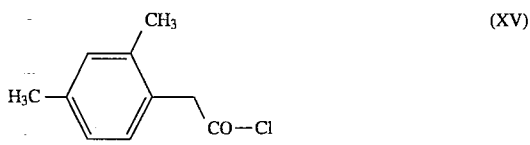

(Chem. Reviews 52, 237–416 (1953); Bhattacharya, Indien J. Chem. 6, 341–5, 1968) or when acylamino acids of the formula (IIa)

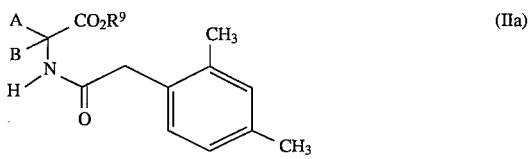

in which

A and B have the abovementioned meaning and $R^9$ represents hydrogen are esterified (Chem. Ind. (London) 1568 (1968)).

Compounds of the formula (IIa) can be obtained, for example, from 2,4-dimethylacetyl chloride, of the formula (XV), and amino acids of the formula (XIVa) by the method of Schotten-Baumann (Organikum [Laboratory Practical in Organic Chemistry], 9th edition, 446 (1970) VEB Deutscher Verlag der Wissenschaften, Berlin).

Furthermore, the starting substances of the formula (II)

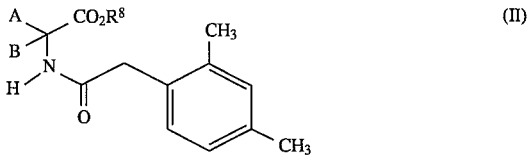

in which

A, B and $R^8$ have the abovementioned meaning which are used in the above process (A) can be prepared when aminonitriles of the formula (XVI)

  (XVI)

in which

A and B have the abovementioned meaning,
are reacted with 2,4-dimethylphenylacetyl chloride, of the formula (XV),

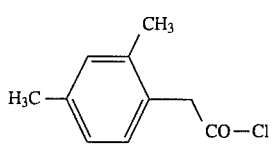  (XV)

to give compounds of the formula (XVII)

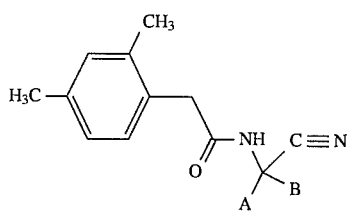  (XVII)

in which

A and B have the abovementioned meaning,
and these compounds are subsequently subjected to alcoholysis in sulphuric acid.

Some of the compounds of the formula (XVII) are also known and the subject-matter of a German Patent Application by the applicant company which has hitherto not been disclosed (P 42 36 400).

The following compounds of the formula (Ia) may be mentioned individually in addition to the compounds mentioned in the preparation examples:

TABLE 1

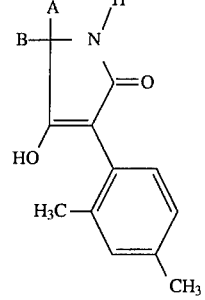  I-a

| A | B |
|---|---|
| $CH_3$ | $C_2H_5$ |
| $CH_3$ | $C_3H_7$-n |
| $CH_3$ | $C_3H_7$-i |
| $CH_3$ | $C_4H_9$-n |
| $CH_3$ | $C_4H_9$-i |
| $CH_3$ | $C_4H_9$-s |
| $CH_3$ | $C_4H_9$-t |
| $CH_3$ | $C_5H_{11}$ |
| $CH_3$ | $C_5H_{11}$-i |
| $C_2H_5$ | $C_2H_5$ |
| $C_3H_7$ | $C_3H_7$ |
| $C_3H_7$-i | $C_3H_7$-i |

TABLE 1-continued

I-a

| A | B |
|---|---|
| $-(CH_2)_2-$ | |
| $-(CH_2)_4-$ | |
| $-(CH_2)_5-$ | |
| $-(CH_2)_6-$ | |
| $-(CH_2)_7-$ | |

The following compounds of the formula (Ib) may be mentioned individually in addition to the compounds mentioned in the preparation examples:

TABLE 2

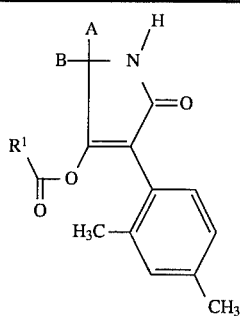  I-b

| A | B | $R^1$ |
|---|---|---|
| $CH_3$ | $C_2H_5$ | $CH_3$ |
| $CH_3$ | $C_2H_5$ | $C_2H_5$ |
| $CH_3$ | $C_2H_5$ | $C_3H_7$-n |
| $CH_3$ | $C_2H_5$ | $C_3H_7$-i |
| $CH_3$ | $C_2H_5$ | $C_4H_9$-n |
| $CH_3$ | $C_2H_5$ | $C_4H_9$-i |
| $CH_3$ | $C_2H_5$ | $C_4H_9$-t |
| $CH_3$ | $C_2H_5$ | $-C(CH_3)_2-C_2H_5$ |
| $CH_3$ | $C_2H_5$ | $-C(CH_3)_2-C_3H_7$-i |
| $CH_3$ | $C_2H_5$ | $-C(CH_3)_2-CH_2-Cl$ |
| $CH_3$ | $C_2H_5$ | $-C(CH_3)_2-CH_2-O-CH_3$ |
| $CH_3$ | $C_2H_5$ | $-CH_2-C_4H_9$-t |
| $CH_3$ | $C_2H_5$ | $-CH-C_4H_9$<br>$\quad\mid$<br>$\quad C_2H_5$ |
| $CH_3$ | $C_2H_5$ | $-CH_2-S-CH_3$ |
| $CH_3$ | $C_2H_5$ | $-CH=C(CH_3)_2$ |
| $CH_3$ | $C_2H_5$ | phenyl |

TABLE 2-continued

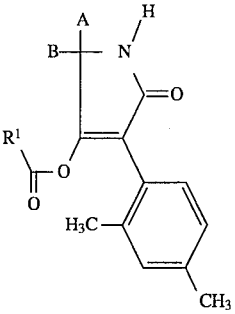

I-b

| A | B | R¹ |
|---|---|---|
| CH₃ | C₂H₅ | 4-Cl-C₆H₄ |
| CH₃ | C₂H₅ | 4-CH₃-C₆H₄ |
| CH₃ | C₂H₅ | 4-NO₂-C₆H₄ |
| CH₃ | C₂H₅ | 4-OCH₃-C₆H₄ |
| CH₃ | C₂H₅ | —CH₂—C₆H₅ |
| CH₃ | C₃H₇ | CH₃ |
| CH₃ | C₃H₇ | C₂H₅ |
| CH₃ | C₃H₇ | C₃H₇-n |
| CH₃ | C₃H₇ | C₃H₇-i |
| CH₃ | C₃H₇ | C₄H₉-n |
| CH₃ | C₃H₇ | C₄H₉-i |
| CH₃ | C₃H₇ | C₄H₉-t |
| CH₃ | C₃H₇ | —C(CH₃)₂—C₂H₅ |
| CH₃ | C₃H₇ | —C(CH₃)₂—C₃H₇-i |
| CH₃ | C₃H₇ | —C(CH₃)₂—CH₂—Cl |
| CH₃ | C₃H₇ | —C(CH₃)₂—CH₂—O—CH₃ |
| CH₃ | C₃H₇ | —CH₂—C₄H₉-t |
| CH₃ | C₃H₇ | —CH(C₂H₅)—C₄H₉ |
| CH₃ | C₃H₇ | —CH₂—S—CH₃ |
| CH₃ | C₃H₇ | —CH=C(CH₃)₂ |
| CH₃ | C₃H₇ | C₆H₅ |
| CH₃ | C₃H₇ | 4-Cl-C₆H₄ |
| CH₃ | C₃H₇ | 4-CH₃-C₆H₄ |
| CH₃ | C₃H₇ | 4-NO₂-C₆H₄ |
| CH₃ | C₃H₇ | 4-OCH₃-C₆H₄ |
| CH₃ | C₃H₇ | —CH₂—C₆H₅ |
| CH₃ | C₃H₇-i | CH₃ |
| CH₃ | C₃H₇-i | C₂H₅ |
| CH₃ | C₃H₇-i | C₃H₇-n |
| CH₃ | C₃H₇-i | C₃H₇-i |
| CH₃ | C₃H₇-i | C₄H₉-n |
| CH₃ | C₃H₇-i | C₄H₉-i |
| CH₃ | C₃H₇-i | C₄H₉-t |
| CH₃ | C₃H₇-i | —C(CH₃)₂—C₂H₅ |
| CH₃ | C₃H₇-i | —C(CH₃)₂—C₃H₇-i |
| CH₃ | C₃H₇-i | —C(CH₃)₂—CH₂—Cl |
| CH₃ | C₃H₇-i | —C(CH₃)₂—CH₂—O—CH₃ |
| CH₃ | C₃H₇-i | —CH₂—C₄H₉-t |
| CH₃ | C₃H₇-i | —CH(C₂H₅)—C₄H₉ |
| CH₃ | C₃H₇-i | —CH₂—S—CH₃ |
| CH₃ | C₃H₇-i | —CH=C(CH₃)₂ |
| CH₃ | C₃H₇-i | C₆H₅ |
| CH₃ | C₃H₇-i | 4-Cl-C₆H₄ |
| CH₃ | C₃H₇-i | 4-CH₃-C₆H₄ |
| CH₃ | C₃H₇-i | 4-NO₂-C₆H₄ |
| CH₃ | C₃H₇-i | 4-OCH₃-C₆H₄ |

TABLE 2-continued

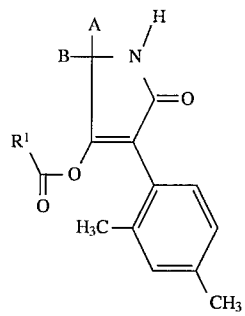

I-b

| A | B | R¹ |
|---|---|---|
| CH₃ | C₃H₇-i | —CH₂—C₆H₅ |
| CH₃ | C₄H₉ | CH₃ |
| CH₃ | C₄H₉ | C₂H₅ |
| CH₃ | C₄H₉ | C₃H₇-n |
| CH₃ | C₄H₉ | C₃H₇-i |
| CH₃ | C₄H₉ | C₄H₉-n |
| CH₃ | C₄H₉ | C₄H₉-i |
| CH₃ | C₄H₉ | C₄H₉-t |
| CH₃ | C₄H₉ | —C(CH₃)₂—C₂H₅ |
| CH₃ | C₄H₉ | —C(CH₃)₂—C₃H₇-i |
| CH₃ | C₄H₉ | —C(CH₃)₂—CH₂—Cl |
| CH₃ | C₄H₉ | —C(CH₃)₂—CH₂—O—CH₃ |
| CH₃ | C₄H₉ | —CH₂—C₄H₉-t |
| CH₃ | C₄H₉ | —CH(C₂H₅)—C₄H₉ |
| CH₃ | C₄H₉ | —CH₂—S—CH₃ |
| CH₃ | C₄H₉ | —CH=C(CH₃)₂ |
| CH₃ | C₄H₉ | —C₆H₅ |
| CH₃ | C₄H₉ | —C₆H₄—Cl (p) |
| CH₃ | C₄H₉ | —C₆H₄—CH₃ (p) |
| CH₃ | C₄H₉ | —C₆H₄—NO₂ (p) |
| CH₃ | C₄H₉ | —C₆H₄—OCH₃ (p) |
| CH₃ | C₄H₉ | —CH₂—C₆H₅ |
| CH₃ | C₄H₉-i | CH₃ |
| CH₃ | C₄H₉-i | C₂H₅ |
| CH₃ | C₄H₉-i | C₃H₇-n |
| CH₃ | C₄H₉-i | C₃H₇-i |
| CH₃ | C₄H₉-i | C₄H₉-n |
| CH₃ | C₄H₉-i | C₄H₉-i |
| CH₃ | C₄H₉-i | C₄H₉-t |
| CH₃ | C₄H₉-i | —C(CH₃)₂—C₂H₅ |
| CH₃ | C₄H₉-i | —C(CH₃)₂—C₃H₇-i |
| CH₃ | C₄H₉-i | —C(CH₃)₂—CH₂—Cl |
| CH₃ | C₄H₉-i | —C(CH₃)₂—CH₂—O—CH₃ |
| CH₃ | C₄H₉-i | —CH₂—C₄H₉-t |
| CH₃ | C₄H₉-i | —CH(C₂H₅)—C₄H₉ |
| CH₃ | C₄H₉-i | —CH₂—S—CH₃ |
| CH₃ | C₄H₉-i | —CH=C(CH₃)₂ |
| CH₃ | C₄H₉-i | —C₆H₅ |
| CH₃ | C₄H₉-i | —C₆H₄—Cl (p) |
| CH₃ | C₄H₉-i | —C₆H₄—CH₃ (p) |
| CH₃ | C₄H₉-i | —C₆H₄—NO₂ (p) |
| CH₃ | C₄H₉-i | —C₆H₄—OCH₃ (p) |
| CH₃ | C₄H₉-i | —CH₂—C₆H₅ |
| CH₃ | —C₄H₉-s | CH₃ |
| CH₃ | —C₄H₉-s | C₂H₅ |
| CH₃ | —C₄H₉-s | C₃H₇-n |
| CH₃ | —C₄H₉-s | C₃H₇-i |
| CH₃ | —C₄H₉-s | C₄H₉-n |
| CH₃ | —C₄H₉-s | C₄H₉-i |
| CH₃ | —C₄H₉-s | C₄H₉-t |
| CH₃ | —C₄H₉-s | —C(CH₃)₂—C₂H₅ |
| CH₃ | —C₄H₉-s | —C(CH₃)₂—C₃H₇-i |
| CH₃ | —C₄H₉-s | —C(CH₃)₂—CH₂—Cl |
| CH₃ | —C₄H₉-s | —C(CH₃)₂—CH₂—O—CH₃ |
| CH₃ | —C₄H₉-s | —CH₂—C₄H₉-t |
| CH₃ | —C₄H₉-s | —CH(C₂H₅)—C₄H₉ |

TABLE 2-continued

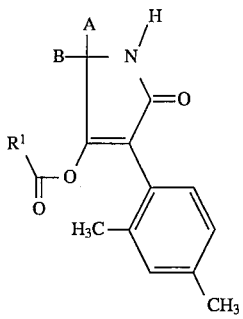

I-b

| A | B | R¹ |
|---|---|---|
| CH₃ | —C₄H₉-s | —CH₂—S—CH₃ |
| CH₃ | —C₄H₉-s | —CH=C(CH₃)₂ |
| CH₃ | —C₄H₉-s | —C₆H₅ (phenyl) |
| CH₃ | —C₄H₉-s | 4-Cl-C₆H₄ |
| CH₃ | —C₄H₉-s | 4-CH₃-C₆H₄ |
| CH₃ | —C₄H₉-s | 4-NO₂-C₆H₄ |
| CH₃ | —C₄H₉-s | 4-OCH₃-C₆H₄ |
| CH₃ | —C₄H₉-s | —CH₂—C₆H₅ |
| CH₃ | C₄H₉-t | CH₃ |
| CH₃ | C₄H₉-t | C₂H₅ |
| CH₃ | C₄H₉-t | C₃H₇-n |
| CH₃ | C₄H₉-t | C₃H₇-i |
| CH₃ | C₄H₉-t | C₄H₉-n |
| CH₃ | C₄H₉-t | C₄H₉-i |
| CH₃ | C₄H₉-t | C₄H₉-t |
| CH₃ | C₄H₉-t | —C(CH₃)₂—C₂H₅ |
| CH₃ | C₄H₉-t | —C(CH₃)₂—C₃H₇-i |
| CH₃ | C₄H₉-t | —C(CH₃)₂—CH₂—Cl |
| CH₃ | C₄H₉-t | —C(CH₃)₂—CH₂—O—CH₃ |
| CH₃ | C₄H₉-t | —CH₂—C₄H₉-t |
| CH₃ | C₄H₉-t | —CH(C₄H₉)(C₂H₅) |
| CH₃ | C₄H₉-t | —CH₂—S—CH₃ |
| CH₃ | C₄H₉-t | —CH=C(CH₃)₂ |
| CH₃ | C₄H₉-t | —C₆H₅ (phenyl) |

TABLE 2-continued

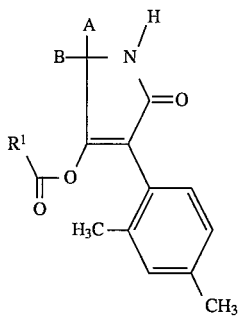

I-b

| A | B | R¹ |
|---|---|---|
| CH₃ | C₄H₉-t | 4-Cl-C₆H₄ |
| CH₃ | C₄H₉-t | 4-CH₃-C₆H₄ |
| CH₃ | C₄H₉-t | 4-NO₂-C₆H₄ |
| CH₃ | C₄H₉-t | 4-OCH₃-C₆H₄ |
| CH₃ | C₄H₉-t | —CH₂—C₆H₅ |
| C₂H₅ | C₂H₅ | CH₃ |
| C₂H₅ | C₂H₅ | C₂H₅ |
| C₂H₅ | C₂H₅ | C₃H₇-n |
| C₂H₅ | C₂H₅ | C₃H₇-i |
| C₂H₅ | C₂H₅ | C₄H₉-n |
| C₂H₅ | C₂H₅ | C₄H₉-i |
| C₂H₅ | C₂H₅ | C₄H₉-t |
| C₂H₅ | C₂H₅ | —C(CH₃)₂—C₂H₅ |
| C₂H₅ | C₂H₅ | —C(CH₃)₂—C₃H₇-i |
| C₂H₅ | C₂H₅ | —C(CH₃)₂—CH₂—Cl |
| C₂H₅ | C₂H₅ | —C(CH₃)₂—CH₂—O—CH₃ |
| C₂H₅ | C₂H₅ | —CH₂—C₄H₉-t |
| C₂H₅ | C₂H₅ | —CH(C₄H₉)(C₂H₅) |
| C₂H₅ | C₂H₅ | —CH₂—S—CH₃ |
| C₂H₅ | C₂H₅ | —CH=C(CH₃)₂ |
| C₂H₅ | C₂H₅ | —C₆H₅ (phenyl) |
| C₂H₅ | C₂H₅ | 4-Cl-C₆H₄ |
| C₂H₅ | C₂H₅ | 4-CH₃-C₆H₄ |

TABLE 2-continued

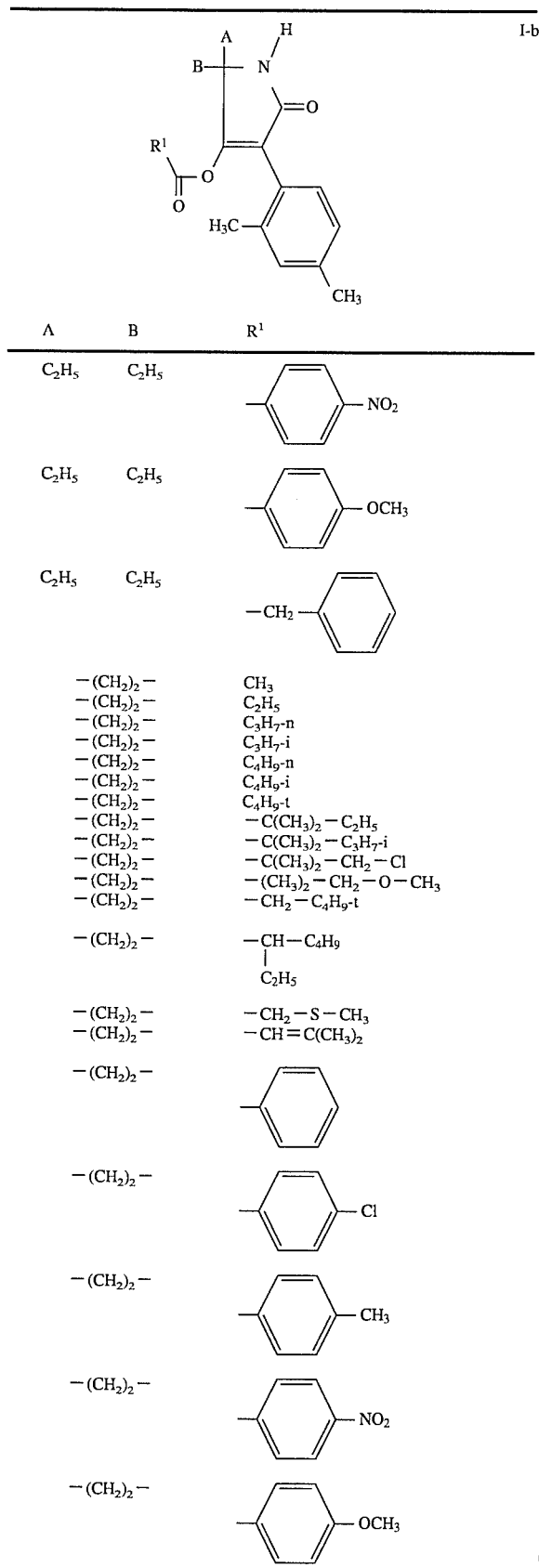

| A | B | R¹ |
|---|---|---|
| C₂H₅ | C₂H₅ | -C₆H₄-NO₂ (p) |
| C₂H₅ | C₂H₅ | -C₆H₄-OCH₃ (p) |
| C₂H₅ | C₂H₅ | -CH₂-C₆H₅ |
| -(CH₂)₂- | | CH₃ |
| -(CH₂)₂- | | C₂H₅ |
| -(CH₂)₂- | | C₃H₇-n |
| -(CH₂)₂- | | C₃H₇-i |
| -(CH₂)₂- | | C₄H₉-n |
| -(CH₂)₂- | | C₄H₉-i |
| -(CH₂)₂- | | C₄H₉-t |
| -(CH₂)₂- | | -C(CH₃)₂-C₂H₅ |
| -(CH₂)₂- | | -C(CH₃)₂-C₃H₇-i |
| -(CH₂)₂- | | -C(CH₃)₂-CH₂-Cl |
| -(CH₂)₂- | | -(CH₃)₂-CH₂-O-CH₃ |
| -(CH₂)₂- | | -CH₂-C₄H₉-t |
| -(CH₂)₂- | | -CH(C₄H₉)-C₂H₅ |
| -(CH₂)₂- | | -CH₂-S-CH₃ |
| -(CH₂)₂- | | -CH=C(CH₃)₂ |
| -(CH₂)₂- | | -C₆H₅ |
| -(CH₂)₂- | | -C₆H₄-Cl (p) |
| -(CH₂)₂- | | -C₆H₄-CH₃ (p) |
| -(CH₂)₂- | | -C₆H₄-NO₂ (p) |
| -(CH₂)₂- | | -C₆H₄-OCH₃ (p) |

TABLE 2-continued

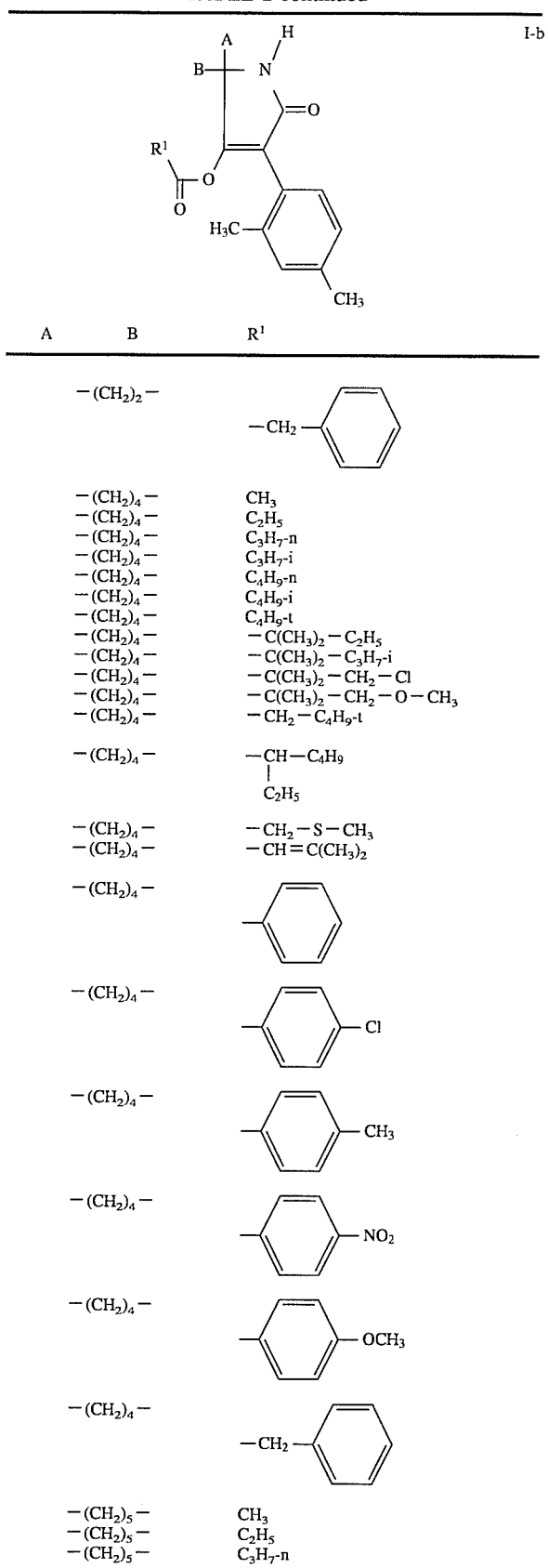

| A | B | R¹ |
|---|---|---|
| -(CH₂)₂- | | -CH₂-C₆H₅ |
| -(CH₂)₄- | | CH₃ |
| -(CH₂)₄- | | C₂H₅ |
| -(CH₂)₄- | | C₃H₇-n |
| -(CH₂)₄- | | C₃H₇-i |
| -(CH₂)₄- | | C₄H₉-n |
| -(CH₂)₄- | | C₄H₉-i |
| -(CH₂)₄- | | C₄H₉-t |
| -(CH₂)₄- | | -C(CH₃)₂-C₂H₅ |
| -(CH₂)₄- | | -C(CH₃)₂-C₃H₇-i |
| -(CH₂)₄- | | -C(CH₃)₂-CH₂-Cl |
| -(CH₂)₄- | | -C(CH₃)₂-CH₂-O-CH₃ |
| -(CH₂)₄- | | -CH₂-C₄H₉-t |
| -(CH₂)₄- | | -CH(C₄H₉)-C₂H₅ |
| -(CH₂)₄- | | -CH₂-S-CH₃ |
| -(CH₂)₄- | | -CH=C(CH₃)₂ |
| -(CH₂)₄- | | -C₆H₅ |
| -(CH₂)₄- | | -C₆H₄-Cl (p) |
| -(CH₂)₄- | | -C₆H₄-CH₃ (p) |
| -(CH₂)₄- | | -C₆H₄-NO₂ (p) |
| -(CH₂)₄- | | -C₆H₄-OCH₃ (p) |
| -(CH₂)₄- | | -CH₂-C₆H₅ |
| -(CH₂)₅- | | CH₃ |
| -(CH₂)₅- | | C₂H₅ |
| -(CH₂)₅- | | C₃H₇-n |

TABLE 2-continued

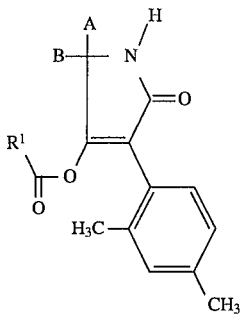 I-b

| A | B | R¹ |
|---|---|---|
| | —(CH₂)₅— | $C_3H_7$-i |
| | —(CH₂)₅— | $C_4H_9$-n |
| | —(CH₂)₅— | $C_4H_9$-i |
| | —(CH₂)₅— | $C_4H_9$-t |
| | —(CH₂)₅— | —C(CH₃)₂—C₂H₅ |
| | —(CH₂)₅— | —C(CH₃)₂—C₃H₇-i |
| | —(CH₂)₅— | —C(CH₃)₂—CH₂—Cl |
| | —(CH₂)₅— | —C(CH₃)₂—CH₂—O—CH₃ |
| | —(CH₂)₅— | —CH₂—C₄H₉-t |
| | —(CH₂)₅— | —CH(C₂H₅)—C₄H₉ |
| | —(CH₂)₅— | —CH₂—S—CH₃ |
| | —(CH₂)₅— | —CH=C(CH₃)₂ |
| | —(CH₂)₅— | —C₆H₅ |
| | —(CH₂)₅— | —C₆H₄-Cl (p) |
| | —(CH₂)₅— | —C₆H₄-CH₃ (p) |
| | —(CH₂)₅— | —C₆H₄-NO₂ (p) |
| | —(CH₂)₅— | —C₆H₄-OCH₃ (p) |
| | —(CH₂)₅— | —CH₂—C₆H₅ |
| | —(CH₂)₆— | CH₃ |
| | —(CH₂)₆— | C₂H₅ |
| | —(CH₂)₆— | $C_3H_7$-n |
| | —(CH₂)₆— | $C_3H_7$-i |
| | —(CH₂)₆— | $C_4H_9$-n |
| | —(CH₂)₆— | $C_4H_9$-i |
| | —(CH₂)₆— | $C_4H_9$-t |
| | —(CH₂)₆— | —C(CH₃)₂—C₂H₅ |
| | —(CH₂)₆— | —C(CH₃)₂—C₃H₇-i |
| | —(CH₂)₆— | —C(CH₃)₂—CH₂—Cl |
| | —(CH₂)₆— | —C(CH₃)₂—CH₂—O—CH₃ |
| | —(CH₂)₆— | —CH₂—C₄H₉-t |

TABLE 2-continued

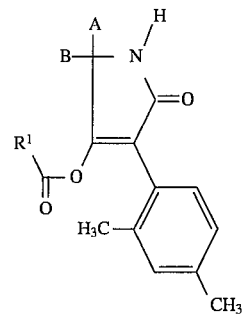 I-b

| A | B | R¹ |
|---|---|---|
| | —(CH₂)₆— | —CH(C₂H₅)—C₄H₉ |
| | —(CH₂)₆— | —CH₂—S—CH₃ |
| | —(CH₂)₆— | —CH=C(CH₃)₂ |
| | —(CH₂)₆— | —C₆H₅ |
| | —(CH₂)₆— | —C₆H₄-Cl (p) |
| | —(CH₂)₆— | —C₆H₄-CH₃ (p) |
| | —(CH₂)₆— | —C₆H₄-NO₂ (p) |
| | —(CH₂)₆— | —C₆H₄-OCH₃ (p) |
| | —(CH₂)₆— | —CH₂—C₆H₅ |
| | —(CH₂)₇— | CH₃ |
| | —(CH₂)₇— | C₂H₅ |
| | —(CH₂)₇— | $C_3H_7$-n |
| | —(CH₂)₇— | $C_3H_7$-i |
| | —(CH₂)₇— | $C_4H_9$-n |
| | —(CH₂)₇— | $C_4H_9$-i |
| | —(CH₂)₇— | $C_4H_9$-t |
| | —(CH₂)₇— | —C(CH₃)₂—C₂H₅ |
| | —(CH₂)₇— | —C(CH₃)₂—C₃H₇-i |
| | —(CH₂)₇— | —C(CH₃)₂—CH₂—Cl |
| | —(CH₂)₇— | —C(CH₃)₂—CH₂—O—CH₃ |
| | —(CH₂)₇— | —CH₂—C₄H₉-t |
| | —(CH₂)₇— | —CH(C₂H₅)—C₄H₉ |
| | —(CH₂)₇— | —CH₂—S—CH₃ |
| | —(CH₂)₇— | —CH=C(CH₃)₂ |
| | —(CH₂)₇— | —C₆H₅ |

TABLE 2-continued

I-b

Structure: Compound with formula showing A-B-C(N-H)=C(C=O)-C(=C-O-C(=O)-R¹)-phenyl ring with 2-CH₃ and 4-CH₃ substituents.

| A | B | R¹ |
|---|---|---|
| —(CH₂)₇— | | —C₆H₄—Cl (para) |
| —(CH₂)₇— | | —C₆H₄—CH₃ (para) |
| —(CH₂)₇— | | —C₆H₄—NO₂ (para) |
| —(CH₂)₇— | | —C₆H₄—OCH₃ (para) |
| —(CH₂)₇— | | —CH₂—C₆H₅ |

The following compounds of the formula (Ic) may be mentioned individually in addition to the compounds mentioned in the preparation examples:

TABLE 3

I-c

Structure: Compound with formula showing A-B-C(N-H)=C(C=O)-C(=C-O-C(=L)-M-R²)-phenyl ring with 2-CH₃ and 4-CH₃ substituents.

| A | B | L | M | R² |
|---|---|---|---|---|
| CH₃ | C₂H₅ | O | O | CH₃ |
| CH₃ | C₂H₅ | O | O | —C₂H₅ |
| CH₃ | C₂H₅ | O | O | —C₃H₇ |
| CH₃ | C₂H₅ | O | O | —C₃H₇-i |
| CH₃ | C₂H₅ | O | O | —C₄H₉-i |
| CH₃ | C₂H₅ | O | O | —C₄H₉-s |
| CH₃ | C₂H₅ | O | O | —C₄H₉-t |
| CH₃ | C₂H₅ | O | O | —CH₂—C₄H₉-t |

TABLE 3-continued

I-c

| A | B | L | M | R² |
|---|---|---|---|---|
| CH₃ | C₂H₅ | O | O | cyclohexyl |
| CH₃ | C₂H₅ | O | O | phenyl |
| CH₃ | C₂H₅ | O | O | —CH₂—phenyl |
| CH₃ | C₂H₅ | O | S | CH₃ |
| CH₃ | C₂H₅ | O | S | —C₂H₅ |
| CH₃ | C₂H₅ | O | S | —C₃H₇ |
| CH₃ | C₂H₅ | O | S | —C₃H₇-i |
| CH₃ | C₂H₅ | O | S | —C₄H₉-i |
| CH₃ | C₂H₅ | O | S | —C₄H₉-s |
| CH₃ | C₂H₅ | O | S | —C₄H₉-t |
| CH₃ | C₂H₅ | O | S | —CH₂—C₄H₉-t |
| CH₃ | C₃H₇ | O | O | CH₃ |
| CH₃ | C₃H₇ | O | O | —C₂H₅ |
| CH₃ | C₃H₇ | O | O | —C₃H₇ |
| CH₃ | C₃H₇ | O | O | —C₃H₇-i |
| CH₃ | C₃H₇ | O | O | —C₄H₉-i |
| CH₃ | C₃H₇ | O | O | —C₄H₉-s |
| CH₃ | C₃H₇ | O | O | —C₄H₉-t |
| CH₃ | C₃H₇ | O | O | —CH₂—C₄H₉-t |
| CH₃ | C₃H₇ | O | O | cyclohexyl |
| CH₃ | C₃H₇ | O | O | phenyl |
| CH₃ | C₃H₇ | O | O | —CH₂—phenyl |
| CH₃ | C₃H₇ | O | S | CH₃ |
| CH₃ | C₃H₇ | O | S | —C₂H₅ |
| CH₃ | C₃H₇ | O | S | —C₃H₇ |
| CH₃ | C₃H₇ | O | S | —C₃H₇-i |
| CH₃ | C₃H₇ | O | S | —C₄H₉-i |
| CH₃ | C₃H₇ | O | S | —C₄H₉-s |
| CH₃ | C₃H₇ | O | S | —C₄H₉-t |
| CH₃ | C₃H₇ | O | S | —CH₂—C₄H₉-t |
| CH₃ | C₃H₇-i | O | O | CH₃ |
| CH₃ | C₃H₇-i | O | O | —C₂H₅ |
| CH₃ | C₃H₇-i | O | O | —C₃H₇ |
| CH₃ | C₃H₇-i | O | O | —C₃H₇-i |
| CH₃ | C₃H₇-i | O | O | —C₄H₉-i |

TABLE 3-continued

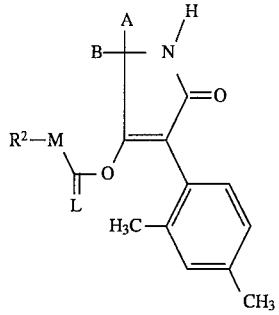

I-c

| A | B | L | M | R² |
|---|---|---|---|---|
| CH₃ | C₃H₇-i | O | O | —C₄H₉-s |
| CH₃ | C₃H₇-i | O | O | —C₄H₉-t |
| CH₃ | C₃H₇-i | O | O | —CH₂—C₄H₉-t |
| CH₃ | C₃H₇-i | O | O | cyclohexyl |
| CH₃ | C₃H₇-i | O | O | phenyl |
| CH₃ | C₃H₇-i | O | O | —CH₂—phenyl |
| CH₃ | C₃H₇-i | O | S | CH₃ |
| CH₃ | C₃H₇-i | O | S | —C₂H₅ |
| CH₃ | C₃H₇-i | O | S | —C₃H₇ |
| CH₃ | C₃H₇-i | O | S | —C₃H₇-i |
| CH₃ | C₃H₇-i | O | S | —C₄H₉-i |
| CH₃ | C₃H₇-i | O | S | —C₄H₉-s |
| CH₃ | C₃H₇-i | O | S | —C₄H₉-t |
| CH₃ | C₃H₇-i | O | S | —CH₂—C₄H₉-t |
| CH₃ | C₄H₉ | O | O | CH₃ |
| CH₃ | C₄H₉ | O | O | —C₂H₅ |
| CH₃ | C₄H₉ | O | O | —C₃H₇ |
| CH₃ | C₄H₉ | O | O | —C₃H₇-i |
| CH₃ | C₄H₉ | O | O | —C₄H₉-i |
| CH₃ | C₄H₉ | O | O | —C₄H₉-s |
| CH₃ | C₄H₉ | O | O | —C₄H₉-t |
| CH₃ | C₄H₉ | O | O | —CH₂—C₄H₉-t |
| CH₃ | C₄H₉ | O | O | cyclohexyl |
| CH₃ | C₄H₉ | O | O | phenyl |
| CH₃ | C₄H₉ | O | O | —CH₂—phenyl |
| CH₃ | C₄H₉ | O | S | CH₃ |
| CH₃ | C₄H₉ | O | S | —C₂H₅ |
| CH₃ | C₄H₉ | O | S | —C₃H₇ |
| CH₃ | C₄H₉ | O | S | —C₃H₇-i |
| CH₃ | C₄H₉ | O | S | —C₄H₉-i |
| CH₃ | C₄H₉ | O | S | —C₄H₉-s |
| CH₃ | C₄H₉ | O | S | —C₄H₉-t |
| CH₃ | C₄H₉ | O | S | —CH₂—C₄H₉-t |
| CH₃ | C₄H₉-i | O | O | CH₃ |

TABLE 3-continued

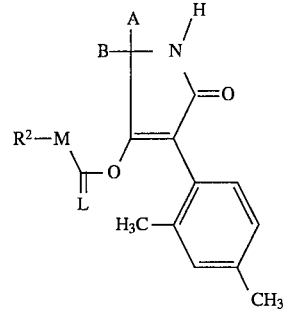

I-c

| A | B | L | M | R² |
|---|---|---|---|---|
| CH₃ | C₄H₉-i | O | O | —C₂H₅ |
| CH₃ | C₄H₉-i | O | O | —C₃H₇ |
| CH₃ | C₄H₉-i | O | O | —C₃H₇-i |
| CH₃ | C₄H₉-i | O | O | —C₄H₉-i |
| CH₃ | C₄H₉-i | O | O | —C₄H₉-s |
| CH₃ | C₄H₉-i | O | O | —C₄H₉-t |
| CH₃ | C₄H₉-i | O | O | —CH₂—C₄H₉-t |
| CH₃ | C₄H₉-i | O | O | cyclohexyl |
| CH₃ | C₄H₉-i | O | O | phenyl |
| CH₃ | C₄H₉-i | O | O | —CH₂—phenyl |
| CH₃ | C₄H₉-i | O | S | CH₃ |
| CH₃ | C₄H₉-i | O | S | —C₂H₅ |
| CH₃ | C₄H₉-i | O | S | —C₃H₇ |
| CH₃ | C₄H₉-i | O | S | —C₃H₇-i |
| CH₃ | C₄H₉-i | O | S | —C₄H₉-i |
| CH₃ | C₄H₉-i | O | S | —C₄H₉-s |
| CH₃ | C₄H₉-i | O | S | —C₄H₉-t |
| CH₃ | C₄H₉-i | O | S | —CH₂—C₄H₉-t |
| CH₃ | C₄H₉-s | O | O | CH₃ |
| CH₃ | C₄H₉-s | O | O | —C₂H₅ |
| CH₃ | C₄H₉-s | O | O | —C₃H₇ |
| CH₃ | C₄H₉-s | O | O | —C₃H₇-i |
| CH₃ | C₄H₉-s | O | O | —C₄H₉-i |
| CH₃ | C₄H₉-s | O | O | —C₄H₉-s |
| CH₃ | C₄H₉-s | O | O | —C₄H₉-t |
| CH₃ | C₄H₉-s | O | O | —CH₂—C₄H₉-t |
| CH₃ | C₄H₉-s | O | O | cyclohexyl |
| CH₃ | C₄H₉-s | O | O | phenyl |
| CH₃ | C₄H₉-s | O | O | —CH₂—phenyl |
| CH₃ | C₄H₉-s | O | S | CH₃ |
| CH₃ | C₄H₉-s | O | S | —C₂H₅ |
| CH₃ | C₄H₉-s | O | S | —C₃H₇ |
| CH₃ | C₄H₉-s | O | S | —C₃H₇-i |
| CH₃ | C₄H₉-s | O | S | —C₄H₉-i |

TABLE 3-continued

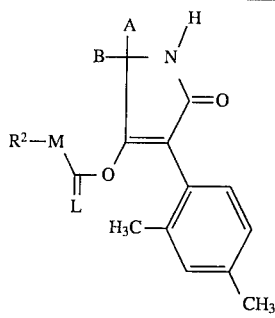

I-c

| A | B | L | M | R² |
|---|---|---|---|---|
| CH₃ | C₄H₉-s | O | S | —C₄H₉-s |
| CH₃ | C₄H₉-s | O | S | —C₄H₉-t |
| CH₃ | C₄H₉-s | O | S | —CH₂—C₄H₉-t |
| CH₃ | C₄H₉-t | O | O | CH₃ |
| CH₃ | C₄H₉-t | O | O | —C₂H₅ |
| CH₃ | C₄H₉-t | O | O | —C₃H₇ |
| CH₃ | C₄H₉-t | O | O | —C₃H₇-i |
| CH₃ | C₄H₉-t | O | O | —C₄H₉-i |
| CH₃ | C₄H₉-t | O | O | —C₄H₉-s |
| CH₃ | C₄H₉-t | O | O | —C₄H₉-t |
| CH₃ | C₄H₉-t | O | O | —CH₂—C₄H₉-t |
| CH₃ | C₄H₉-t | O | O | cyclohexyl |
| CH₃ | C₄H₉-t | O | O | phenyl |
| CH₃ | C₄H₉-t | O | O | —CH₂-phenyl |
| CH₃ | C₄H₉-t | O | S | CH₃ |
| CH₃ | C₄H₉-t | O | S | —C₂H₅ |
| CH₃ | C₄H₉-t | O | S | —C₃H₇ |
| CH₃ | C₄H₉-t | O | S | —C₃H₇-i |
| CH₃ | C₄H₉-t | O | S | —C₄H₉-i |
| CH₃ | C₄H₉-t | O | S | —C₄H₉-s |
| CH₃ | C₄H₉-t | O | S | —C₄H₉-t |
| CH₃ | C₄H₉-t | O | S | —CH₂—C₄H₉-t |
| C₂H₅ | C₂H₅ | O | O | CH₃ |
| C₂H₅ | C₂H₅ | O | O | —C₂H₅ |
| C₂H₅ | C₂H₅ | O | O | —C₃H₇ |
| C₂H₅ | C₂H₅ | O | O | —C₃H₇-i |
| C₂H₅ | C₂H₅ | O | O | —C₄H₉-i |
| C₂H₅ | C₂H₅ | O | O | —C₄H₉-s |
| C₂H₅ | C₂H₅ | O | O | —C₄H₉-t |
| C₂H₅ | C₂H₅ | O | O | —CH₂—C₄H₉-t |
| C₂H₅ | C₂H₅ | O | O | cyclohexyl |
| C₂H₅ | C₂H₅ | O | O | phenyl |
| C₂H₅ | C₂H₅ | O | O | —CH₂-phenyl |
| C₂H₅ | C₂H₅ | O | S | CH₃ |

TABLE 3-continued

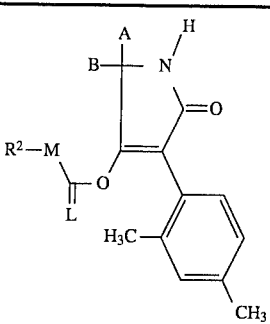

I-c

| A | B | L | M | R² |
|---|---|---|---|---|
| C₂H₅ | C₂H₅ | O | S | —C₂H₅ |
| C₂H₅ | C₂H₅ | O | S | —C₃H₇ |
| C₂H₅ | C₂H₅ | O | S | —C₃H₇-i |
| C₂H₅ | C₂H₅ | O | S | —C₄H₉-i |
| C₂H₅ | C₂H₅ | O | S | —C₄H₉-s |
| C₂H₅ | C₂H₅ | O | S | —C₄H₉-t |
| C₂H₅ | C₂H₅ | O | S | —CH₂—C₄H₉-t |
| —(CH₂)₂— | | O | O | CH₃ |
| —(CH₂)₂— | | O | O | —C₂H₅ |
| —(CH₂)₂— | | O | O | —C₃H₇ |
| —(CH₂)₂— | | O | O | —C₃H₇-i |
| —(CH₂)₂— | | O | O | —C₄H₉-i |
| —(CH₂)₂— | | O | O | —C₄H₉-s |
| —(CH₂)₂— | | O | O | —C₄H₉-t |
| —(CH₂)₂— | | O | O | —CH₂—C₄H₉-t |
| —(CH₂)₂— | | O | O | cyclohexyl |
| —(CH₂)₂— | | O | O | phenyl |
| —(CH₂)₂— | | O | O | —CH₂-phenyl |
| —(CH₂)₂— | | O | S | CH₃ |
| —(CH₂)₂— | | O | S | —C₂H₅ |
| —(CH₂)₂— | | O | S | —C₃H₇ |
| —(CH₂)₂— | | O | S | —C₃H₇-i |
| —(CH₂)₂— | | O | S | —C₄H₉-i |
| —(CH₂)₂— | | O | S | —C₄H₉-s |
| —(CH₂)₂— | | O | S | —C₄H₉-t |
| —(CH₂)₂— | | O | S | —CH₂—C₄H₉-t |
| —(CH₂)₄— | | O | O | CH₃ |
| —(CH₂)₄— | | O | O | —C₂H₅ |
| —(CH₂)₄— | | O | O | —C₃H₇ |
| —(CH₂)₄— | | O | O | —C₃H₇-i |
| —(CH₂)₄— | | O | O | —C₄H₉-i |
| —(CH₂)₄— | | O | O | —C₄H₉-s |
| —(CH₂)₄— | | O | O | —C₄H₉-t |
| —(CH₂)₄— | | O | O | —CH₂—C₄H₉-t |
| —(CH₂)₄— | | O | O | cyclohexyl |
| —(CH₂)₄— | | O | O | phenyl |

TABLE 3-continued

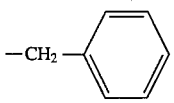

I-c

| A | B | L | M | R² |
|---|---|---|---|---|
| —(CH₂)₄— | | O | O | —CH₂—C₆H₅ |
| —(CH₂)₄— | | O | S | CH₃ |
| —(CH₂)₄— | | O | S | —C₂H₅ |
| —(CH₂)₄— | | O | S | —C₃H₇ |
| —(CH₂)₄— | | O | S | —C₃H₇-i |
| —(CH₂)₄— | | O | S | —C₄H₉-i |
| —(CH₂)₄— | | O | S | —C₄H₉-s |
| —(CH₂)₄— | | O | S | —C₄H₉-t |
| —(CH₂)₄— | | O | S | —CH₂—C₄H₉-t |
| —(CH₂)₅— | | O | O | CH₃ |
| —(CH₂)₅— | | O | O | —C₂H₅ |
| —(CH₂)₅— | | O | O | —C₃H₇ |
| —(CH₂)₅— | | O | O | —C₃H₇-i |
| —(CH₂)₅— | | O | O | —C₄H₉-i |
| —(CH₂)₅— | | O | O | —C₄H₉-s |
| —(CH₂)₅— | | O | O | —C₄H₉-t |
| —(CH₂)₅— | | O | O | —CH₂—C₄H₉-t |
| —(CH₂)₅— | | O | O | cyclohexyl |
| —(CH₂)₅— | | O | O | phenyl |
| —(CH₂)₅— | | O | O | —CH₂—C₆H₅ |
| —(CH₂)₅— | | O | S | CH₃ |
| —(CH₂)₅— | | O | S | —C₂H₅ |
| —(CH₂)₅— | | O | S | —C₃H₇ |
| —(CH₂)₅— | | O | S | —C₃H₇-i |
| —(CH₂)₅— | | O | S | —C₄H₉-i |
| —(CH₂)₅— | | O | S | —C₄H₉-s |
| —(CH₂)₅— | | O | S | —C₄H₉-t |
| —(CH₂)₅— | | O | S | —CH₂—C₄H₉-t |
| —(CH₂)₆— | | O | O | CH₃ |
| —(CH₂)₆— | | O | O | —C₂H₅ |
| —(CH₂)₆— | | O | O | —C₃H₇ |
| —(CH₂)₆— | | O | O | —C₃H₇-i |
| —(CH₂)₆— | | O | O | —C₄H₉-i |
| —(CH₂)₆— | | O | O | —C₄H₉-s |
| —(CH₂)₆— | | O | O | —C₄H₉-t |
| —(CH₂)₆— | | O | O | —CH₂—C₄H₉-t |
| —(CH₂)₆— | | O | O | cyclohexyl |
| —(CH₂)₆— | | O | O | phenyl |
| —(CH₂)₆— | | O | O | —CH₂—C₆H₅ |
| —(CH₂)₆— | | O | S | CH₃ |
| —(CH₂)₆— | | O | S | —C₂H₅ |
| —(CH₂)₆— | | O | S | —C₃H₇ |
| —(CH₂)₆— | | O | S | —C₃H₇-i |
| —(CH₂)₆— | | O | S | —C₄H₉-i |
| —(CH₂)₆— | | O | S | —C₄H₉-s |
| —(CH₂)₆— | | O | S | —C₄H₉-t |
| —(CH₂)₆— | | O | S | —CH₂—C₄H₉-t |
| —(CH₂)₇— | | O | O | CH₃ |
| —(CH₂)₇— | | O | O | —C₂H₅ |
| —(CH₂)₇— | | O | O | —C₃H₇ |
| —(CH₂)₇— | | O | O | —C₃H₇-i |
| —(CH₂)₇— | | O | O | —C₄H₉-i |
| —(CH₂)₇— | | O | O | —C₄H₉-s |
| —(CH₂)₇— | | O | O | —C₄H₉-t |
| —(CH₂)₇— | | O | O | —CH₂—C₄H₉-t |
| —(CH₂)₇— | | O | O | cyclohexyl |
| —(CH₂)₇— | | O | O | phenyl |
| —(CH₂)₇— | | O | O | —CH₂—C₆H₅ |
| —(CH₂)₇— | | O | S | CH₃ |
| —(CH₂)₇— | | O | S | —C₂H₅ |
| —(CH₂)₇— | | O | S | —C₃H₇ |
| —(CH₂)₇— | | O | S | —C₃H₇-i |
| —(CH₂)₇— | | O | S | —C₄H₉-i |
| —(CH₂)₇— | | O | S | —C₄H₉-s |
| —(CH₂)₇— | | O | S | —C₄H₉-t |
| —(CH₂)₇— | | O | S | —CH₂—C₄H₉-t |

The following compounds of the formula (Id) may be mentioned individually in addition to the compounds mentioned in the preparation examples:

TABLE 4

I-d

Structure: B-C(A)-NH-C(=O)-C(=C-O-SO2-R³)-(2-CH3,4-CH3-phenyl)

| A | B | R³ |
|---|---|---|
| CH₃ | C₂H₅ | CH₃ |
| CH₃ | C₃H₇-n | CH₃ |
| CH₃ | C₃H₇-i | CH₃ |
| CH₃ | C₄H₉-n | CH₃ |
| CH₃ | C₄H₉-i | CH₃ |
| CH₃ | C₄H₉-s | CH₃ |
| CH₃ | C₄H₉-t | CH₃ |
| CH₃ | C₅H₁₁ | CH₃ |
| CH₃ | C₅H₁₁-i | CH₃ |
| C₂H₅ | C₂H₅ | CH₃ |
| C₃H₇-n | C₃H₇ | CH₃ |
| C₃H₇-i | C₃H₇-i | CH₃ |
| —(CH₂)₂— | | CH₃ |
| —(CH₂)₄— | | CH₃ |
| —(CH₂)₅— | | CH₃ |
| —(CH₂)₆— | | CH₃ |
| —(CH₂)₇— | | CH₃ |

The following compounds of the formula (Ie) may be mentioned individually in addition to the compounds mentioned in the preparation examples:

TABLE 5

I-e

Structure: B-C(A)-NH-C(=O)-C(=C-O-P(=L)(R⁴)(R⁵))-(2-CH3,4-CH3-phenyl)

| A | B | L | R⁴ | R⁵ |
|---|---|---|---|---|
| CH₃ | C₂H₅ | O | CH₃ | —O—CH₃ |
| CH₃ | C₂H₅ | O | CH₃ | —O—C₂H₅ |
| CH₃ | C₂H₅ | O | CH₃ | —O—C₃H₇ |
| CH₃ | C₂H₅ | O | CH₃ | —O—C₃H₇-i |
| CH₃ | C₂H₅ | O | CH₃ | —O—C₄H₉-i |
| CH₃ | C₂H₅ | O | CH₃ | —O—C₄H₉-s |
| CH₃ | C₂H₅ | O | CH₃ | —O—C₄H₉-t |
| CH₃ | C₂H₅ | O | CH₃ | —O—CH₂—C₄H₉-t |
| CH₃ | C₂H₅ | O | CH₃ | —O—cyclohexyl |
| CH₃ | C₂H₅ | O | CH₃ | —O—phenyl |

TABLE 5-continued

I-e

| A | B | L | R⁴ | R⁵ |
|---|---|---|---|---|
| CH₃ | C₂H₅ | O | CH₃ | —O—CH₂—phenyl |
| CH₃ | C₂H₅ | O | CH₃ | —S—CH₃ |
| CH₃ | C₂H₅ | O | CH₃ | —S—C₂H₅ |
| CH₃ | C₂H₅ | O | CH₃ | —S—C₃H₇ |
| CH₃ | C₂H₅ | O | CH₃ | —S—C₃H₇-i |
| CH₃ | C₂H₅ | O | CH₃ | —S—C₄H₉-i |
| CH₃ | C₂H₅ | O | CH₃ | —S—C₄H₉-s |
| CH₃ | C₂H₅ | O | CH₃ | —S—C₄H₉-t |
| CH₃ | C₂H₅ | O | CH₃ | —S—CH₂—C₄H₉-t |
| CH₃ | C₂H₅ | O | C₂H₅ | —O—CH₃ |
| CH₃ | C₂H₅ | O | C₂H₅ | —O—C₂H₅ |
| CH₃ | C₂H₅ | O | C₂H₅ | —O—C₃H₇ |
| CH₃ | C₂H₅ | O | C₂H₅ | —O—C₃H₇-i |
| CH₃ | C₂H₅ | O | C₂H₅ | —O—C₄H₉-i |
| CH₃ | C₂H₅ | O | C₂H₅ | —O—C₄H₉-s |
| CH₃ | C₂H₅ | O | C₂H₅ | —O—C₄H₉-t |
| CH₃ | C₂H₅ | O | C₂H₅ | —O—CH₂—C₄H₉-t |
| CH₃ | C₂H₅ | O | C₂H₅ | —O—cyclohexyl |
| CH₃ | C₂H₅ | O | C₂H₅ | —O—phenyl |
| CH₃ | C₂H₅ | O | C₂H₅ | —O—CH₂—phenyl |
| CH₃ | C₂H₅ | O | C₂H₅ | —S—CH₃ |
| CH₃ | C₂H₅ | O | C₂H₅ | —S—C₂H₅ |
| CH₃ | C₂H₅ | O | C₂H₅ | —S—C₃H₇ |
| CH₃ | C₂H₅ | O | C₂H₅ | —S—C₃H₇-i |
| CH₃ | C₂H₅ | O | C₂H₅ | —S—C₄H₉-i |
| CH₃ | C₂H₅ | O | C₂H₅ | —S—C₄H₉-s |
| CH₃ | C₂H₅ | O | C₂H₅ | —S—C₄H₉-t |
| CH₃ | C₂H₅ | O | C₂H₅ | —S—CH₂—C₄H₉-t |
| CH₃ | C₃H₇-i | O | CH₃ | —O—CH₃ |
| CH₃ | C₃H₇-i | O | CH₃ | —O—C₂H₅ |
| CH₃ | C₃H₇-i | O | CH₃ | —O—C₃H₇ |
| CH₃ | C₃H₇-i | O | CH₃ | —O—C₃H₇-i |
| CH₃ | C₃H₇-i | O | CH₃ | —O—C₄H₉-i |
| CH₃ | C₃H₇-i | O | CH₃ | —O—C₄H₉-s |
| CH₃ | C₃H₇-i | O | CH₃ | —O—C₄H₉-t |
| CH₃ | C₃H₇-i | O | CH₃ | —O—CH₂—C₄H₉-t |
| CH₃ | C₃H₇-i | O | CH₃ | —O—cyclohexyl |

TABLE 5-continued

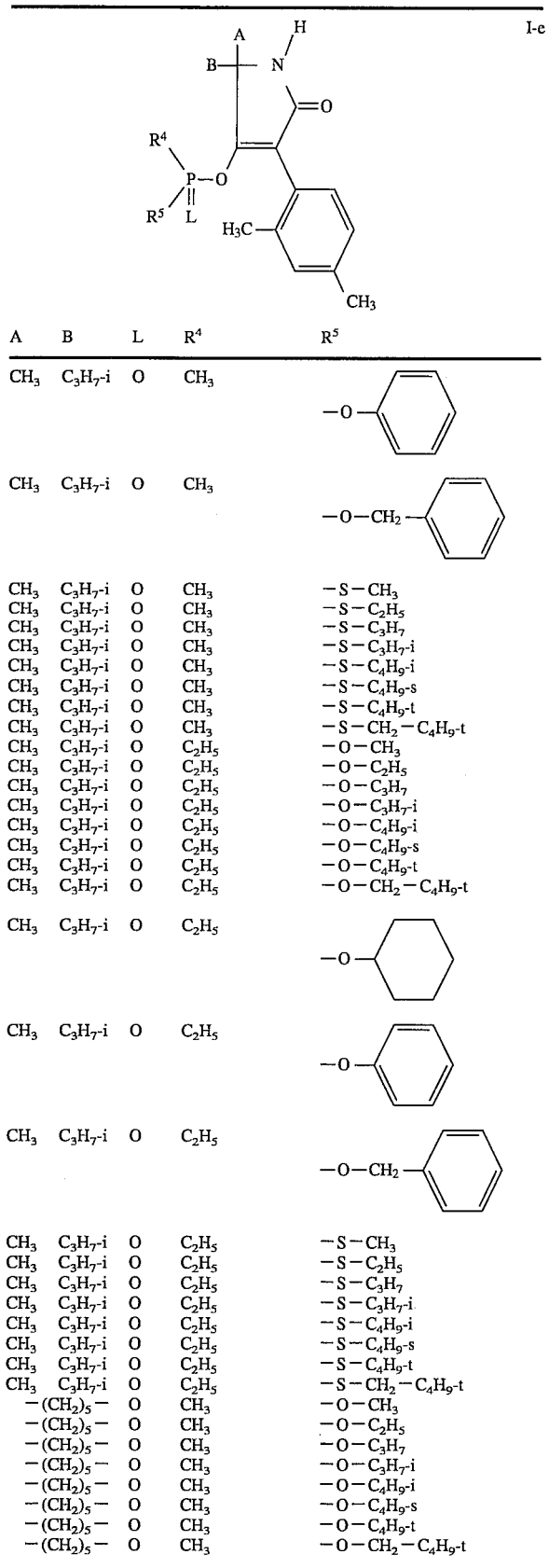

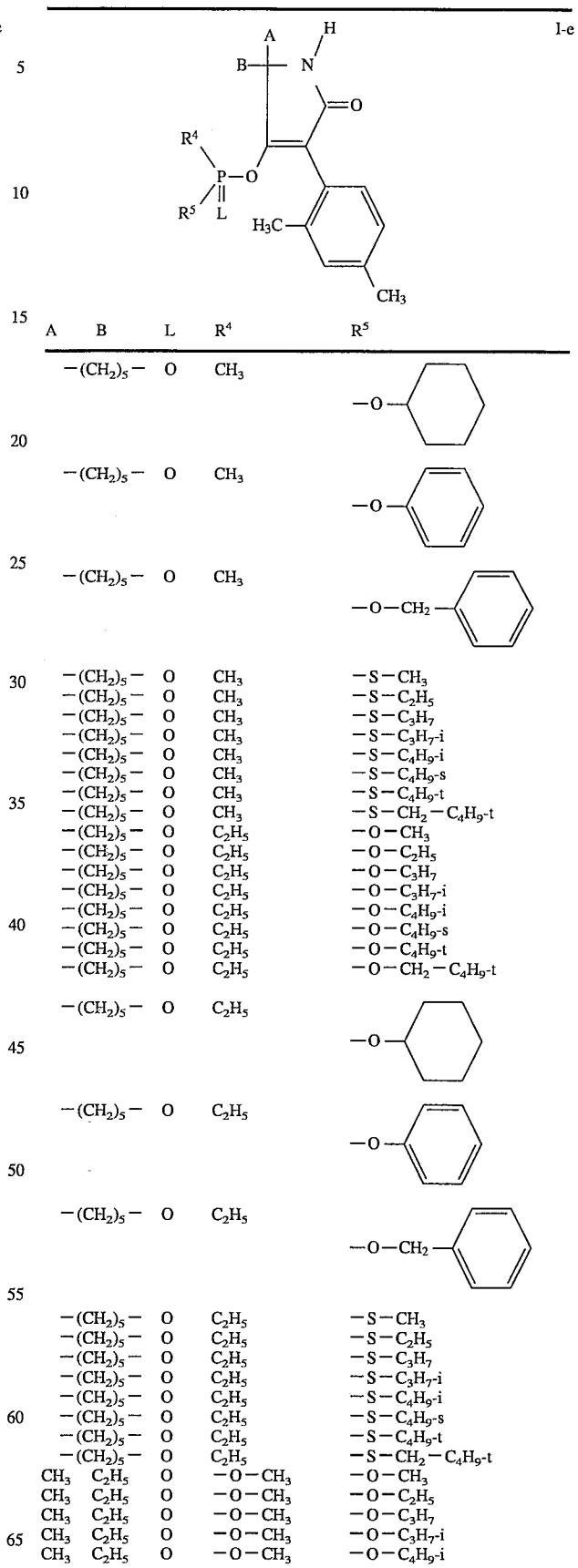

| A | B | L | R⁴ | R⁵ |
|---|---|---|---|---|
| CH₃ | C₃H₇-i | O | CH₃ | —O—C₆H₅ |
| CH₃ | C₃H₇-i | O | CH₃ | —O—CH₂—C₆H₅ |
| CH₃ | C₃H₇-i | O | CH₃ | —S—CH₃ |
| CH₃ | C₃H₇-i | O | CH₃ | —S—C₂H₅ |
| CH₃ | C₃H₇-i | O | CH₃ | —S—C₃H₇ |
| CH₃ | C₃H₇-i | O | CH₃ | —S—C₃H₇-i |
| CH₃ | C₃H₇-i | O | CH₃ | —S—C₄H₉-i |
| CH₃ | C₃H₇-i | O | CH₃ | —S—C₄H₉-s |
| CH₃ | C₃H₇-i | O | CH₃ | —S—C₄H₉-t |
| CH₃ | C₃H₇-i | O | CH₃ | —S—CH₂—C₄H₉-t |
| CH₃ | C₃H₇-i | O | C₂H₅ | —O—CH₃ |
| CH₃ | C₃H₇-i | O | C₂H₅ | —O—C₂H₅ |
| CH₃ | C₃H₇-i | O | C₂H₅ | —O—C₃H₇ |
| CH₃ | C₃H₇-i | O | C₂H₅ | —O—C₃H₇-i |
| CH₃ | C₃H₇-i | O | C₂H₅ | —O—C₄H₉-i |
| CH₃ | C₃H₇-i | O | C₂H₅ | —O—C₄H₉-s |
| CH₃ | C₃H₇-i | O | C₂H₅ | —O—C₄H₉-t |
| CH₃ | C₃H₇-i | O | C₂H₅ | —O—CH₂—C₄H₉-t |
| CH₃ | C₃H₇-i | O | C₂H₅ | —O—C₆H₁₁ (cyclohexyl) |
| CH₃ | C₃H₇-i | O | C₂H₅ | —O—C₆H₅ |
| CH₃ | C₃H₇-i | O | C₂H₅ | —O—CH₂—C₆H₅ |
| CH₃ | C₃H₇-i | O | C₂H₅ | —S—CH₃ |
| CH₃ | C₃H₇-i | O | C₂H₅ | —S—C₂H₅ |
| CH₃ | C₃H₇-i | O | C₂H₅ | —S—C₃H₇ |
| CH₃ | C₃H₇-i | O | C₂H₅ | —S—C₃H₇-i |
| CH₃ | C₃H₇-i | O | C₂H₅ | —S—C₄H₉-i |
| CH₃ | C₃H₇-i | O | C₂H₅ | —S—C₄H₉-s |
| CH₃ | C₃H₇-i | O | C₂H₅ | —S—C₄H₉-t |
| CH₃ | C₃H₇-i | O | C₂H₅ | —S—CH₂—C₄H₉-t |
| —(CH₂)₅— | | O | CH₃ | —O—CH₃ |
| —(CH₂)₅— | | O | CH₃ | —O—C₂H₅ |
| —(CH₂)₅— | | O | CH₃ | —O—C₃H₇ |
| —(CH₂)₅— | | O | CH₃ | —O—C₃H₇-i |
| —(CH₂)₅— | | O | CH₃ | —O—C₄H₉-i |
| —(CH₂)₅— | | O | CH₃ | —O—C₄H₉-s |
| —(CH₂)₅— | | O | CH₃ | —O—C₄H₉-t |
| —(CH₂)₅— | | O | CH₃ | —O—CH₂—C₄H₉-t |
| —(CH₂)₅— | | O | CH₃ | —O—C₆H₁₁ (cyclohexyl) |
| —(CH₂)₅— | | O | CH₃ | —O—C₆H₅ |
| —(CH₂)₅— | | O | CH₃ | —O—CH₂—C₆H₅ |
| —(CH₂)₅— | | O | CH₃ | —S—CH₃ |
| —(CH₂)₅— | | O | CH₃ | —S—C₂H₅ |
| —(CH₂)₅— | | O | CH₃ | —S—C₃H₇ |
| —(CH₂)₅— | | O | CH₃ | —S—C₃H₇-i |
| —(CH₂)₅— | | O | CH₃ | —S—C₄H₉-i |
| —(CH₂)₅— | | O | CH₃ | —S—C₄H₉-s |
| —(CH₂)₅— | | O | CH₃ | —S—C₄H₉-t |
| —(CH₂)₅— | | O | CH₃ | —S—CH₂—C₄H₉-t |
| —(CH₂)₅— | | O | C₂H₅ | —O—CH₃ |
| —(CH₂)₅— | | O | C₂H₅ | —O—C₂H₅ |
| —(CH₂)₅— | | O | C₂H₅ | —O—C₃H₇ |
| —(CH₂)₅— | | O | C₂H₅ | —O—C₃H₇-i |
| —(CH₂)₅— | | O | C₂H₅ | —O—C₄H₉-i |
| —(CH₂)₅— | | O | C₂H₅ | —O—C₄H₉-s |
| —(CH₂)₅— | | O | C₂H₅ | —O—C₄H₉-t |
| —(CH₂)₅— | | O | C₂H₅ | —O—CH₂—C₄H₉-t |
| —(CH₂)₅— | | O | C₂H₅ | —O—C₆H₁₁ (cyclohexyl) |
| —(CH₂)₅— | | O | C₂H₅ | —O—C₆H₅ |
| —(CH₂)₅— | | O | C₂H₅ | —O—CH₂—C₆H₅ |
| —(CH₂)₅— | | O | C₂H₅ | —S—CH₃ |
| —(CH₂)₅— | | O | C₂H₅ | —S—C₂H₅ |
| —(CH₂)₅— | | O | C₂H₅ | —S—C₃H₇ |
| —(CH₂)₅— | | O | C₂H₅ | —S—C₃H₇-i |
| —(CH₂)₅— | | O | C₂H₅ | —S—C₄H₉-i |
| —(CH₂)₅— | | O | C₂H₅ | —S—C₄H₉-s |
| —(CH₂)₅— | | O | C₂H₅ | —S—C₄H₉-t |
| —(CH₂)₅— | | O | C₂H₅ | —S—CH₂—C₄H₉-t |
| CH₃ | C₂H₅ | O | —O—CH₃ | —O—CH₃ |
| CH₃ | C₂H₅ | O | —O—CH₃ | —O—C₂H₅ |
| CH₃ | C₂H₅ | O | —O—CH₃ | —O—C₃H₇ |
| CH₃ | C₂H₅ | O | —O—CH₃ | —O—C₃H₇-i |
| CH₃ | C₂H₅ | O | —O—CH₃ | —O—C₄H₉-i |

TABLE 5-continued

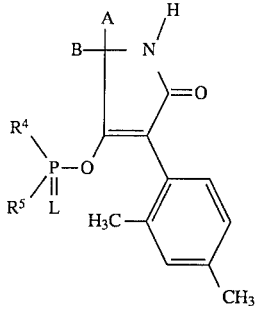

I-c

| A | B | L | R⁴ | R⁵ |
|---|---|---|---|---|
| CH₃ | C₂H₅ | O | —O—CH₃ | —O—C₄H₉-s |
| CH₃ | C₂H₅ | O | —O—CH₃ | —O—C₄H₉-t |
| CH₃ | C₂H₅ | O | —O—CH₃ | —O—CH₂—C₄H₉-t |
| CH₃ | C₂H₅ | O | —O—CH₃ | —O—cyclohexyl |
| CH₃ | C₂H₅ | O | —O—CH₃ | —O—phenyl |
| CH₃ | C₂H₅ | O | —O—CH₃ | —O—CH₂—phenyl |
| CH₃ | C₂H₅ | O | —O—CH₃ | —S—CH₃ |
| CH₃ | C₂H₅ | O | —O—CH₃ | —S—C₂H₅ |
| CH₃ | C₂H₅ | O | —O—CH₃ | —S—C₃H₇ |
| CH₃ | C₂H₅ | O | —O—CH₃ | —S—C₃H₇-i |
| CH₃ | C₂H₅ | O | —O—CH₃ | —S—C₄H₉-i |
| CH₃ | C₂H₅ | O | —O—CH₃ | —S—C₄H₉-s |
| CH₃ | C₂H₅ | O | —O—CH₃ | —S—C₄H₉-t |
| CH₃ | C₂H₅ | O | —O—CH₃ | —S—CH₂—C₄H₉-t |
| CH₃ | C₂H₅ | O | —O—C₂H₅ | —O—CH₃ |
| CH₃ | C₂H₅ | O | —O—C₂H₅ | —O—C₂H₅ |
| CH₃ | C₂H₅ | O | —O—C₂H₅ | —O—C₃H₇ |
| CH₃ | C₂H₅ | O | —O—C₂H₅ | —O—C₃H₇-i |
| CH₃ | C₂H₅ | O | —O—C₂H₅ | —O—C₄H₉-i |
| CH₃ | C₂H₅ | O | —O—C₂H₅ | —O—C₄H₉-s |
| CH₃ | C₂H₅ | O | —O—C₂H₅ | —O—C₄H₉-t |
| CH₃ | C₂H₅ | O | —O—C₂H₅ | —O—CH₂—C₄H₉-t |
| CH₃ | C₂H₅ | O | —O—C₂H₅ | —O—cyclohexyl |
| CH₃ | C₂H₅ | O | —O—C₂H₅ | —O—phenyl |
| CH₃ | C₂H₅ | O | —O—C₂H₅ | —O—CH₂—phenyl |
| CH₃ | C₂H₅ | O | —O—C₂H₅ | —S—CH₃ |
| CH₃ | C₂H₅ | O | —O—C₂H₅ | —S—C₂H₅ |
| CH₃ | C₂H₅ | O | —O—C₂H₅ | —S—C₃H₇ |
| CH₃ | C₂H₅ | O | —O—C₂H₅ | —S—C₃H₇-i |
| CH₃ | C₂H₅ | O | —O—C₂H₅ | —S—C₄H₉-i |
| CH₃ | C₂H₅ | O | —O—C₂H₅ | —S—C₄H₉-s |
| CH₃ | C₂H₅ | O | —O—C₂H₅ | —S—C₄H₉-t |
| CH₃ | C₂H₅ | O | —O—C₂H₅ | —S—CH₂—C₄H₉-t |
| CH₃ | C₃H₇-i | O | —O—CH₃ | —O—CH₃ |

TABLE 5-continued

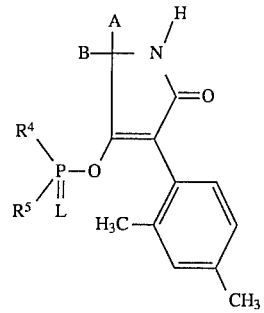

I-c

| A | B | L | R⁴ | R⁵ |
|---|---|---|---|---|
| CH₃ | C₃H₇-i | O | —O—CH₃ | —O—C₂H₅ |
| CH₃ | C₃H₇-i | O | —O—CH₃ | —O—C₃H₇ |
| CH₃ | C₃H₇-i | O | —O—CH₃ | —O—C₃H₇-i |
| CH₃ | C₃H₇-i | O | —O—CH₃ | —O—C₄H₉-s |
| CH₃ | C₃H₇-i | O | —O—CH₃ | —O—C₄H₉-t |
| CH₃ | C₃H₇-i | O | —O—CH₃ | —O—CH₂—C₄H₉-t |
| CH₃ | C₃H₇-i | O | —O—CH₃ | —O—cyclohexyl |
| CH₃ | C₃H₇-i | O | —O—CH₃ | —O—phenyl |
| CH₃ | C₃H₇-i | O | —O—CH₃ | —O—CH₂—phenyl |
| CH₃ | C₃H₇-i | O | —O—CH₃ | —S—CH₃ |
| CH₃ | C₃H₇-i | O | —O—CH₃ | —S—C₂H₅ |
| CH₃ | C₃H₇-i | O | —O—CH₃ | —S—C₃H₇ |
| CH₃ | C₃H₇-i | O | —O—CH₃ | —S—C₃H₇-i |
| CH₃ | C₃H₇-i | O | —O—CH₃ | —S—C₄H₉-i |
| CH₃ | C₃H₇-i | O | —O—CH₃ | —S—C₄H₉-s |
| CH₃ | C₃H₇-i | O | —O—CH₃ | —S—C₄H₉-t |
| CH₃ | C₃H₇-i | O | —O—CH₃ | —S—CH₂—C₄H₉-t |
| CH₃ | C₃H₇-i | O | —O—C₂H₅ | —O—CH₃ |
| CH₃ | C₃H₇-i | O | —O—C₂H₅ | —O—C₂H₅ |
| CH₃ | C₃H₇-i | O | —O—C₂H₅ | —O—C₃H₇ |
| CH₃ | C₃H₇-i | O | —O—C₂H₅ | —O—C₃H₇-i |
| CH₃ | C₃H₇-i | O | —O—C₂H₅ | —O—C₄H₉-i |
| CH₃ | C₃H₇-i | O | —O—C₂H₅ | —O—C₄H₉-s |
| CH₃ | C₃H₇-i | O | —O—C₂H₅ | —O—C₄H₉-t |
| CH₃ | C₃H₇-i | O | —O—C₂H₅ | —O—CH₂—C₄H₉-t |
| CH₃ | C₃H₇-i | O | —O—C₂H₅ | —O—cyclohexyl |
| CH₃ | C₃H₇-i | O | —O—C₂H₅ | —O—phenyl |
| CH₃ | C₃H₇-i | O | —O—C₂H₅ | —O—CH₂—phenyl |
| CH₃ | C₃H₇-i | O | —O—C₂H₅ | —S—CH₃ |
| CH₃ | C₃H₇-i | O | —O—C₂H₅ | —S—C₂H₅ |
| CH₃ | C₃H₇-i | O | —O—C₂H₅ | —S—C₃H₇ |
| CH₃ | C₃H₇-i | O | —O—C₂H₅ | —S—C₃H₇-i |
| CH₃ | C₃H₇-i | O | —O—C₂H₅ | —S—C₄H₉-i |

TABLE 5-continued

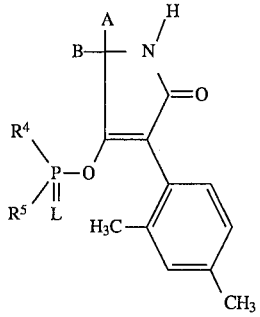

I-e

| A | B | L | R⁴ | R⁵ |
|---|---|---|----|----|
| CH₃ | C₃H₇-i | O | —O—C₂H₅ | —S—C₄H₉-s |
| CH₃ | C₃H₇-i | O | —O—C₂H₅ | —S—C₄H₉-t |
| CH₃ | C₃H₇-i | O | —O—C₂H₅ | —S—CH₂—C₄H₉-t |
| —(CH₂)₅— | | O | —O—CH₃ | —O—CH₃ |
| —(CH₂)₅— | | O | —O—CH₃ | —O—C₂H₅ |
| —(CH₂)₅— | | O | —O—CH₃ | —O—C₃H₇ |
| —(CH₂)₅— | | O | —O—CH₃ | —O—C₃H₇-i |
| —(CH₂)₅— | | O | —O—CH₃ | —O—C₄H₉-i |
| —(CH₂)₅— | | O | —O—CH₃ | —O—C₄H₉-s |
| —(CH₂)₅— | | O | —O—CH₃ | —O—C₄H₉-t |
| —(CH₂)₅— | | O | —O—CH₃ | —O—CH₂—C₄H₉-t |
| —(CH₂)₅— | | O | —O—CH₃ | —O—C₆H₁₁ (cyclohexyl) |
| —(CH₂)₅— | | O | —O—CH₃ | —O—C₆H₅ |
| —(CH₂)₅— | | O | —O—CH₃ | —O—CH₂—C₆H₅ |
| —(CH₂)₅— | | O | —O—CH₃ | —S—CH₃ |
| —(CH₂)₅— | | O | —O—CH₃ | —S—C₂H₅ |
| —(CH₂)₅— | | O | —O—CH₃ | —S—C₃H₇ |
| —(CH₂)₅— | | O | —O—CH₃ | —S—C₃H₇-i |
| —(CH₂)₅— | | O | —O—CH₃ | —S—C₄H₉-i |
| —(CH₂)₅— | | O | —O—CH₃ | —S—C₄H₉-s |
| —(CH₂)₅— | | O | —O—CH₃ | —S—C₄H₉-t |
| —(CH₂)₅— | | O | —O—CH₃ | —S—CH₂—C₄H₉-t |
| —(CH₂)₅— | | O | —O—C₂H₅ | —O—CH₃ |
| —(CH₂)₅— | | O | —O—C₂H₅ | —O—C₂H₅ |
| —(CH₂)₅— | | O | —O—C₂H₅ | —O—C₃H₇ |
| —(CH₂)₅— | | O | —O—C₂H₅ | —O—C₃H₇-i |
| —(CH₂)₅— | | O | —O—C₂H₅ | —O—C₄H₉-i |
| —(CH₂)₅— | | O | —O—C₂H₅ | —O—C₄H₉-s |
| —(CH₂)₅— | | O | —O—C₂H₅ | —O—C₄H₉-t |
| —(CH₂)₅— | | O | —O—C₂H₅ | —O—CH₂—C₄H₉-t |
| —(CH₂)₅— | | O | —O—C₂H₅ | —O—C₆H₁₁ (cyclohexyl) |
| —(CH₂)₅— | | O | —O—C₂H₅ | —O—C₆H₅ |
| —(CH₂)₅— | | O | —O—C₂H₅ | —O—CH₂—C₆H₅ |
| —(CH₂)₅— | | O | —O—C₂H₅ | —S—CH₃ |

TABLE 5-continued

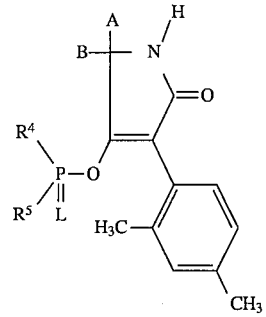

I-e

| A | B | L | R⁴ | R⁵ |
|---|---|---|----|----|
| —(CH₂)₅— | | O | —O—C₂H₅ | —S—C₂H₅ |
| —(CH₂)₅— | | O | —O—C₂H₅ | —S—C₃H₇ |
| —(CH₂)₅— | | O | —O—C₂H₅ | —S—C₃H₇-i |
| —(CH₂)₅— | | O | —O—C₂H₅ | —S—C₄H₉-i |
| —(CH₂)₅— | | O | —O—C₂H₅ | —S—C₄H₉-s |
| —(CH₂)₅— | | O | C₂H₅ | —S—C₄H₉-t |
| —(CH₂)₅— | | O | C₂H₅ | —S—CH₂—C₄H₉-t |
| CH₃ | C₂H₅ | S | CH₃ | —O—CH₃ |
| CH₃ | C₂H₅ | S | CH₃ | —O—C₂H₅ |
| CH₃ | C₂H₅ | S | CH₃ | —O—C₃H₇ |
| CH₃ | C₂H₅ | S | CH₃ | —O—C₃H₇-i |
| CH₃ | C₂H₅ | S | CH₃ | —O—C₄H₉-i |
| CH₃ | C₂H₅ | S | CH₃ | —O—C₄H₉-s |
| CH₃ | C₂H₅ | S | CH₃ | —O—C₄H₉-t |
| CH₃ | C₂H₅ | S | CH₃ | —O—CH₂—C₄H₉-t |
| CH₃ | C₂H₅ | S | CH₃ | —O—C₆H₁₁ (cyclohexyl) |
| CH₃ | C₂H₅ | S | CH₃ | —O—C₆H₅ |
| CH₃ | C₂H₅ | S | CH₃ | —O—CH₂—C₆H₅ |
| CH₃ | C₂H₅ | S | CH₃ | —S—CH₃ |
| CH₃ | C₂H₅ | S | CH₃ | —S—C₂H₅ |
| CH₃ | C₂H₅ | S | CH₃ | —S—C₃H₇ |
| CH₃ | C₂H₅ | S | CH₃ | —S—C₃H₇-i |
| CH₃ | C₂H₅ | S | CH₃ | —S—C₄H₉-i |
| CH₃ | C₂H₅ | S | CH₃ | —S—C₄H₉-s |
| CH₃ | C₂H₅ | S | CH₃ | —S—C₄H₉-t |
| CH₃ | C₂H₅ | S | CH₃ | —S—CH₂—C₄H₉-t |
| CH₃ | C₂H₅ | S | C₂H₅ | —O—CH₃ |
| CH₃ | C₂H₅ | S | C₂H₅ | —O—C₂H₅ |
| CH₃ | C₂H₅ | S | C₂H₅ | —O—C₃H₇ |
| CH₃ | C₂H₅ | S | C₂H₅ | —O—C₃H₇-i |
| CH₃ | C₂H₅ | S | C₂H₅ | —O—C₄H₉-i |
| CH₃ | C₂H₅ | S | C₂H₅ | —O—C₄H₉-s |
| CH₃ | C₂H₅ | S | C₂H₅ | —O—C₄H₉-t |
| CH₃ | C₂H₅ | S | C₂H₅ | —O—CH₂—C₄H₉-t |
| CH₃ | C₂H₅ | S | C₂H₅ | —O—C₆H₁₁ (cyclohexyl) |
| CH₃ | C₂H₅ | S | C₂H₅ | —O—C₆H₅ |

TABLE 5-continued $$\text{I-e}$$

Structure: 2-(2,4-dimethylphenyl) compound with A, B substituents on carbon bearing NH, C=O group, and O-P(=L)(R⁴)(R⁵).

| A | B | L | R⁴ | R⁵ |
|---|---|---|----|----|
| CH₃ | C₂H₅ | S | C₂H₅ | —O—CH₂—C₆H₅ |
| CH₃ | C₂H₅ | S | C₂H₅ | —S—CH₃ |
| CH₃ | C₂H₅ | S | C₂H₅ | —S—C₂H₅ |
| CH₃ | C₂H₅ | S | C₂H₅ | —S—C₃H₇ |
| CH₃ | C₂H₅ | S | C₂H₅ | —S—C₃H₇-i |
| CH₃ | C₂H₅ | S | C₂H₅ | —S—C₄H₉-i |
| CH₃ | C₂H₅ | S | C₂H₅ | —S—C₄H₉-s |
| CH₃ | C₂H₅ | S | C₂H₅ | —S—C₄H₉-t |
| CH₃ | C₂H₅ | S | C₂H₅ | —S—CH₂—C₄H₉-t |
| CH₃ | C₃H₇-i | S | CH₃ | —O—CH₃ |
| CH₃ | C₃H₇-i | S | CH₃ | —O—C₂H₅ |
| CH₃ | C₃H₇-i | S | CH₃ | —O—C₃H₇ |
| CH₃ | C₃H₇-i | S | CH₃ | —O—C₃H₇-i |
| CH₃ | C₃H₇-i | S | CH₃ | —O—C₄H₉-i |
| CH₃ | C₃H₇-i | S | CH₃ | —O—C₄H₉-s |
| CH₃ | C₃H₇-i | S | CH₃ | —O—C₄H₉-t |
| CH₃ | C₃H₇-i | S | CH₃ | —O—CH₂—C₄H₉-t |
| CH₃ | C₃H₇-i | S | CH₃ | —O—C₆H₁₁ (cyclohexyl) |
| CH₃ | C₃H₇-i | S | CH₃ | —O—C₆H₅ |
| CH₃ | C₃H₇-i | S | CH₃ | —O—CH₂—C₆H₅ |
| CH₃ | C₃H₇-i | S | CH₃ | —S—CH₃ |
| CH₃ | C₃H₇-i | S | CH₃ | —S—C₂H₅ |
| CH₃ | C₃H₇-i | S | CH₃ | —S—C₃H₇ |
| CH₃ | C₃H₇-i | S | CH₃ | —S—C₃H₇-i |
| CH₃ | C₃H₇-i | S | CH₃ | —S—C₄H₉-i |
| CH₃ | C₃H₇-i | S | CH₃ | —S—C₄H₉-s |
| CH₃ | C₃H₇-i | S | CH₃ | —S—C₄H₉-t |
| CH₃ | C₃H₇-i | S | CH₃ | —S—CH₂—C₄H₉-t |
| CH₃ | C₃H₇-i | S | C₂H₅ | —O—CH₃ |
| CH₃ | C₃H₇-i | S | C₂H₅ | —O—C₂H₅ |
| CH₃ | C₃H₇-i | S | C₂H₅ | —O—C₃H₇ |
| CH₃ | C₃H₇-i | S | C₂H₅ | —O—C₃H₇-i |
| CH₃ | C₃H₇-i | S | C₂H₅ | —O—C₄H₉-i |
| CH₃ | C₃H₇-i | S | C₂H₅ | —O—C₄H₉-s |
| CH₃ | C₃H₇-i | S | C₂H₅ | —O—C₄H₉-t |
| CH₃ | C₃H₇-i | S | C₂H₅ | —O—CH₂—C₄H₉-t |
| CH₃ | C₃H₇-i | S | C₂H₅ | —O—C₆H₁₁ (cyclohexyl) |
| CH₃ | C₃H₇-i | S | C₂H₅ | —O—C₆H₅ |
| CH₃ | C₃H₇-i | S | C₂H₅ | —O—CH₂—C₆H₅ |
| CH₃ | C₃H₇-i | S | C₂H₅ | —S—CH₃ |
| CH₃ | C₃H₇-i | S | C₂H₅ | —S—C₂H₅ |
| CH₃ | C₃H₇-i | S | C₂H₅ | —S—C₃H₇ |
| CH₃ | C₃H₇-i | S | C₂H₅ | —S—C₃H₇-i |
| CH₃ | C₃H₇-i | S | C₂H₅ | —S—C₄H₉-i |
| CH₃ | C₃H₇-i | S | C₂H₅ | —S—C₄H₉-s |
| CH₃ | C₃H₇-i | S | C₂H₅ | —S—C₄H₉-t |
| CH₃ | C₃H₇-i | S | C₂H₅ | —S—CH₂—C₄H₉-t |
| —(CH₂)₅— | | S | CH₃ | —O—CH₃ |
| —(CH₂)₅— | | S | CH₃ | —O—C₂H₅ |
| —(CH₂)₅— | | S | CH₃ | —O—C₃H₇ |
| —(CH₂)₅— | | S | CH₃ | —O—C₃H₇-i |
| —(CH₂)₅— | | S | CH₃ | —O—C₄H₉-i |
| —(CH₂)₅— | | S | CH₃ | —O—C₄H₉-s |
| —(CH₂)₅— | | S | CH₃ | —O—C₄H₉-t |
| —(CH₂)₅— | | S | CH₃ | —O—CH₂—C₄H₉-t |
| —(CH₂)₅— | | S | CH₃ | —O—C₆H₁₁ (cyclohexyl) |
| —(CH₂)₅— | | S | CH₃ | —O—C₆H₅ |
| —(CH₂)₅— | | S | CH₃ | —O—CH₂—C₆H₅ |
| —(CH₂)₅— | | S | CH₃ | —S—CH₃ |
| —(CH₂)₅— | | S | CH₃ | —S—C₂H₅ |
| —(CH₂)₅— | | S | CH₃ | —S—C₃H₇ |
| —(CH₂)₅— | | S | CH₃ | —S—C₃H₇-i |
| —(CH₂)₅— | | S | CH₃ | —S—C₄H₉-i |
| —(CH₂)₅— | | S | CH₃ | —S—C₄H₉-s |
| —(CH₂)₅— | | S | CH₃ | —S—C₄H₉-t |
| —(CH₂)₅— | | S | CH₃ | —S—CH₂—C₄H₉-t |
| —(CH₂)₅— | | S | C₂H₅ | —O—CH₃ |
| —(CH₂)₅— | | S | C₂H₅ | —O—C₂H₅ |
| —(CH₂)₅— | | S | C₂H₅ | —O—C₃H₇ |
| —(CH₂)₅— | | S | C₂H₅ | —O—C₃H₇-i |
| —(CH₂)₅— | | S | C₂H₅ | —O—C₄H₉-i |
| —(CH₂)₅— | | S | C₂H₅ | —O—C₄H₉-s |
| —(CH₂)₅— | | S | C₂H₅ | —O—C₄H₉-t |
| —(CH₂)₅— | | S | C₂H₅ | —O—CH₂—C₄H₉-t |

TABLE 5-continued

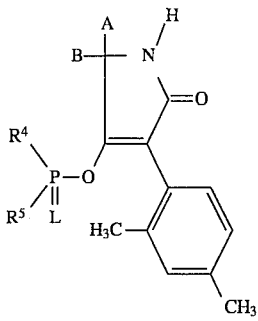

I-e

| A | B | L | R⁴ | R⁵ |
|---|---|---|---|---|
| —(CH$_2$)$_5$— | | S | C$_2$H$_5$ | —O—cyclohexyl |
| —(CH$_2$)$_5$— | | S | C$_2$H$_5$ | —O—phenyl |
| —(CH$_2$)$_5$— | | S | C$_2$H$_5$ | —O—CH$_2$—phenyl |
| —(CH$_2$)$_5$— | | S | C$_2$H$_5$ | —S—CH$_3$ |
| —(CH$_2$)$_5$— | | S | C$_2$H$_5$ | —S—C$_2$H$_5$ |
| —(CH$_2$)$_5$— | | S | C$_2$H$_5$ | —S—C$_3$H$_7$ |
| —(CH$_2$)$_5$— | | S | C$_2$H$_5$ | —S—C$_3$H$_7$-i |
| —(CH$_2$)$_5$— | | S | C$_2$H$_5$ | —S—C$_4$H$_9$-i |
| —(CH$_2$)$_5$— | | S | C$_2$H$_5$ | —S—C$_4$H$_9$-s |
| —(CH$_2$)$_5$— | | S | C$_2$H$_5$ | —S—C$_4$H$_9$-t |
| —(CH$_2$)$_5$— | | S | C$_2$H$_5$ | —S—CH$_2$—C$_4$H$_9$-t |
| CH$_3$ | C$_2$H$_5$ | S | —O—CH$_3$ | —O—CH$_3$ |
| CH$_3$ | C$_2$H$_5$ | S | —O—CH$_3$ | —O—C$_2$H$_5$ |
| CH$_3$ | C$_2$H$_5$ | S | —O—CH$_3$ | —O—C$_3$H$_7$ |
| CH$_3$ | C$_2$H$_5$ | S | —O—CH$_3$ | —O—C$_3$H$_7$-i |
| CH$_3$ | C$_2$H$_5$ | S | —O—CH$_3$ | —O—C$_4$H$_9$-i |
| CH$_3$ | C$_2$H$_5$ | S | —O—CH$_3$ | —O—C$_4$H$_9$-s |
| CH$_3$ | C$_2$H$_5$ | S | —O—CH$_3$ | —O—C$_4$H$_9$-t |
| CH$_3$ | C$_2$H$_5$ | S | —O—CH$_3$ | —O—CH$_2$—C$_4$H$_9$-t |
| CH$_3$ | C$_2$H$_5$ | S | —O—CH$_3$ | —O—cyclohexyl |
| CH$_3$ | C$_2$H$_5$ | S | —O—CH$_3$ | —O—phenyl |
| CH$_3$ | C$_2$H$_5$ | S | —O—CH$_3$ | —O—CH$_2$—phenyl |
| CH$_3$ | C$_2$H$_5$ | S | —O—CH$_3$ | —S—CH$_3$ |
| CH$_3$ | C$_2$H$_5$ | S | —O—CH$_3$ | —S—C$_2$H$_5$ |
| CH$_3$ | C$_2$H$_5$ | S | —O—CH$_3$ | —S—C$_3$H$_7$ |
| CH$_3$ | C$_2$H$_5$ | S | —O—CH$_3$ | —S—C$_3$H$_7$-i |
| CH$_3$ | C$_2$H$_5$ | S | —O—CH$_3$ | —S—C$_4$H$_9$-i |
| CH$_3$ | C$_2$H$_5$ | S | —O—CH$_3$ | —S—C$_4$H$_9$-s |
| CH$_3$ | C$_2$H$_5$ | S | —O—CH$_3$ | —S—C$_4$H$_9$-t |
| CH$_3$ | C$_2$H$_5$ | S | —O—CH$_3$ | —S—CH$_2$—C$_4$H$_9$-t |
| CH$_3$ | C$_2$H$_5$ | S | —O—C$_2$H$_5$ | —O—CH$_3$ |
| CH$_3$ | C$_2$H$_5$ | S | —O—C$_2$H$_5$ | —O—C$_2$H$_5$ |
| CH$_3$ | C$_2$H$_5$ | S | —O—C$_2$H$_5$ | —O—C$_3$H$_7$ |
| CH$_3$ | C$_2$H$_5$ | S | —O—C$_2$H$_5$ | —O—C$_3$H$_7$-i |
| CH$_3$ | C$_2$H$_5$ | S | —O—C$_2$H$_5$ | —O—C$_4$H$_9$-i |

TABLE 5-continued

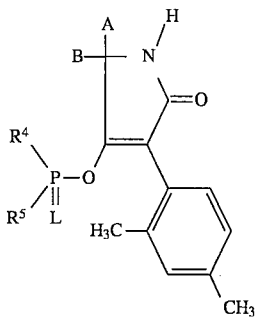

I-e

| A | B | L | R⁴ | R⁵ |
|---|---|---|---|---|
| CH$_3$ | C$_2$H$_5$ | S | —O—C$_2$H$_5$ | —O—C$_4$H$_9$-s |
| CH$_3$ | C$_2$H$_5$ | S | —O—C$_2$H$_5$ | —O—C$_4$H$_9$-t |
| CH$_3$ | C$_2$H$_5$ | S | —O—C$_2$H$_5$ | —O—CH$_2$—C$_4$H$_9$-t |
| CH$_3$ | C$_2$H$_5$ | S | —O—C$_2$H$_5$ | —O—cyclohexyl |
| CH$_3$ | C$_2$H$_5$ | S | —O—C$_2$H$_5$ | —O—phenyl |
| CH$_3$ | C$_2$H$_5$ | S | —O—C$_2$H$_5$ | —O—CH$_2$—phenyl |
| CH$_3$ | C$_2$H$_5$ | S | —O—C$_2$H$_5$ | —S—CH$_3$ |
| CH$_3$ | C$_2$H$_5$ | S | —O—C$_2$H$_5$ | —S—C$_2$H$_5$ |
| CH$_3$ | C$_2$H$_5$ | S | —O—C$_2$H$_5$ | —S—C$_3$H$_7$ |
| CH$_3$ | C$_2$H$_5$ | S | —O—C$_2$H$_5$ | —S—C$_3$H$_7$-i |
| CH$_3$ | C$_2$H$_5$ | S | —O—C$_2$H$_5$ | —S—C$_4$H$_9$-i |
| CH$_3$ | C$_2$H$_5$ | S | —O—C$_2$H$_5$ | —S—C$_4$H$_9$-s |
| CH$_3$ | C$_2$H$_5$ | S | —O—C$_2$H$_5$ | —S—C$_4$H$_9$-t |
| CH$_3$ | C$_2$H$_5$ | S | —O—C$_2$H$_5$ | —S—CH$_2$—C$_4$H$_9$-t |
| CH$_3$ | C$_3$H$_7$-i | S | —O—CH$_3$ | —O—CH$_3$ |
| CH$_3$ | C$_3$H$_7$-i | S | —O—CH$_3$ | —O—C$_2$H$_5$ |
| CH$_3$ | C$_3$H$_7$-i | S | —O—CH$_3$ | —O—C$_3$H$_7$ |
| CH$_3$ | C$_3$H$_7$-i | S | —O—CH$_3$ | —O—C$_3$H$_7$-i |
| CH$_3$ | C$_3$H$_7$-i | S | —O—CH$_3$ | —O—C$_4$H$_9$-i |
| CH$_3$ | C$_3$H$_7$-i | S | —O—CH$_3$ | —O—C$_4$H$_9$-s |
| CH$_3$ | C$_3$H$_7$-i | S | —O—CH$_3$ | —O—C$_4$H$_9$-t |
| CH$_3$ | C$_3$H$_7$-i | S | —O—CH$_3$ | —O—CH$_2$—C$_4$H$_9$-t |
| CH$_3$ | C$_3$H$_7$-i | S | —O—CH$_3$ | —O—cyclohexyl |
| CH$_3$ | C$_3$H$_7$-i | S | —O—CH$_3$ | —O—phenyl |
| CH$_3$ | C$_3$H$_7$-i | S | —O—CH$_3$ | —O—CH$_2$—phenyl |
| CH$_3$ | C$_3$H$_7$-i | S | —O—CH$_3$ | —S—CH$_3$ |
| CH$_3$ | C$_3$H$_7$-i | S | —O—CH$_3$ | —S—C$_2$H$_5$ |
| CH$_3$ | C$_3$H$_7$-i | S | —O—CH$_3$ | —S—C$_3$H$_7$ |
| CH$_3$ | C$_3$H$_7$-i | S | —O—CH$_3$ | —S—C$_3$H$_7$-i |
| CH$_3$ | C$_3$H$_7$-i | S | —O—CH$_3$ | —S—C$_4$H$_9$-i |
| CH$_3$ | C$_3$H$_7$-i | S | —O—CH$_3$ | —S—C$_4$H$_9$-s |
| CH$_3$ | C$_3$H$_7$-i | S | —O—CH$_3$ | —S—C$_4$H$_9$-t |
| CH$_3$ | C$_3$H$_7$-i | S | —O—CH$_3$ | —S—CH$_2$—C$_4$H$_9$-t |
| CH$_3$ | C$_3$H$_7$-i | S | —O—C$_2$H$_5$ | —O—CH$_3$ |

TABLE 5-continued

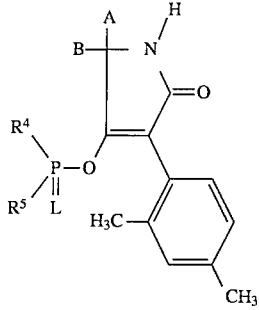

I-e

| A | B | L | R⁴ | R⁵ |
|---|---|---|---|---|
| CH₃ | C₃H₇-i | S | —O—C₂H₅ | —O—C₂H₅ |
| CH₃ | C₃H₇-i | S | —O—C₂H₅ | —O—C₃H₇ |
| CH₃ | C₃H₇-i | S | —O—C₂H₅ | —O—C₃H₇-i |
| CH₃ | C₃H₇-i | S | —O—C₂H₅ | —O—C₄H₉-i |
| CH₃ | C₃H₇-i | S | —O—C₂H₅ | —O—C₄H₉-s |
| CH₃ | C₃H₇-i | S | —O—C₂H₅ | —O—C₄H₉-t |
| CH₃ | C₃H₇-i | S | —O—C₂H₅ | —O—CH₂—C₄H₉-t |
| CH₃ | C₃H₇-i | S | —O—C₂H₅ | —O—cyclohexyl |
| CH₃ | C₃H₇-i | S | —O—C₂H₅ | —O—phenyl |
| CH₃ | C₃H₇-i | S | —O—C₂H₅ | —O—CH₂—phenyl |
| CH₃ | C₃H₇-i | S | —O—C₂H₅ | —S—CH₃ |
| CH₃ | C₃H₇-i | S | —O—C₂H₅ | —S—C₂H₅ |
| CH₃ | C₃H₇-i | S | —O—C₂H₅ | —S—C₃H₇ |
| CH₃ | C₃H₇-i | S | —O—C₂H₅ | —S—C₃H₇-i |
| CH₃ | C₃H₇-i | S | —O—C₂H₅ | —S—C₄H₉-i |
| CH₃ | C₃H₇-i | S | —O—C₂H₅ | —S—C₄H₉-s |
| CH₃ | C₃H₇-i | S | —O—C₂H₅ | —S—C₄H₉-t |
| CH₃ | C₃H₇-i | S | —O—C₂H₅ | —S—CH₂—C₄H₉-t |
| —(CH₂)₅— | | S | —O—CH₃ | —O—CH₃ |
| —(CH₂)₅— | | S | —O—CH₃ | —O—C₂H₅ |
| —(CH₂)₅— | | S | —O—CH₃ | —O—C₃H₇ |
| —(CH₂)₅— | | S | —O—CH₃ | —O—C₃H₇-i |
| —(CH₂)₅— | | S | —O—CH₃ | —O—C₄H₉-i |
| —(CH₂)₅— | | S | —O—CH₃ | —O—C₄H₉-s |
| —(CH₂)₅— | | S | —O—CH₃ | —O—C₄H₉-t |
| —(CH₂)₅— | | S | —O—CH₃ | —O—CH₂—C₄H₉-t |
| —(CH₂)₅— | | S | —O—CH₃ | —O—cyclohexyl |
| —(CH₂)₅— | | S | —O—CH₃ | —O—phenyl |
| —(CH₂)₅— | | S | —O—CH₃ | —O—CH₂—phenyl |

TABLE 5-continued

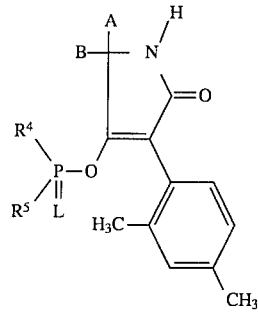

I-e

| A | B | L | R⁴ | R⁵ |
|---|---|---|---|---|
| —(CH₂)₅— | | S | —O—CH₃ | —S—CH₃ |
| —(CH₂)₅— | | S | —O—CH₃ | —S—C₂H₅ |
| —(CH₂)₅— | | S | —O—CH₃ | —S—C₃H₇ |
| —(CH₂)₅— | | S | —O—CH₃ | —S—C₃H₇-i |
| —(CH₂)₅— | | S | —O—CH₃ | —S—C₄H₉-i |
| —(CH₂)₅— | | S | —O—CH₃ | —S—C₄H₉-s |
| —(CH₂)₅— | | S | —O—CH₃ | —S—C₄H₉-t |
| —(CH₂)₅— | | S | —O—CH₃ | —S—CH₂—C₄H₉-t |
| —(CH₂)₅— | | S | —O—C₂H₅ | —O—CH₃ |
| —(CH₂)₅— | | S | —O—C₂H₅ | —O—C₂H₅ |
| —(CH₂)₅— | | S | —O—C₂H₅ | —O—C₃H₇ |
| —(CH₂)₅— | | S | —O—C₂H₅ | —O—C₃H₇-i |
| —(CH₂)₅— | | S | —O—C₂H₅ | —O—C₄H₉-i |
| —(CH₂)₅— | | S | —O—C₂H₅ | —O—C₄H₉-s |
| —(CH₂)₅— | | S | —O—C₂H₅ | —O—C₄H₉-t |
| —(CH₂)₅— | | S | —O—C₂H₅ | —O—CH₂—C₄H₉-t |
| —(CH₂)₅— | | S | —O—C₂H₅ | —O—cyclohexyl |
| —(CH₂)₅— | | S | —O—C₂H₅ | —O—phenyl |
| —(CH₂)₅— | | S | —O—C₂H₅ | —O—CH₂—phenyl |
| —(CH₂)₅— | | S | —O—C₂H₅ | —S—CH₃ |
| —(CH₂)₅— | | S | —O—C₂H₅ | —S—C₂H₅ |
| —(CH₂)₅— | | S | —O—C₂H₅ | —S—C₃H₇ |
| —(CH₂)₅— | | S | —O—C₂H₅ | —S—C₃H₇-i |
| —(CH₂)₅— | | S | —O—C₂H₅ | —S—C₄H₉-i |
| —(CH₂)₅— | | S | —O—C₂H₅ | —S—C₄H₉-s |
| —(CH₂)₅— | | S | —O—C₂H₅ | —S—C₄H₉-t |
| —(CH₂)₅— | | S | —O—C₂H₅ | —S—CH₂—C₄H₉-t |

The following compounds of the formula (If) may be mentioned individually in addition to the compounds mentioned in the preparation examples:

TABLE 6

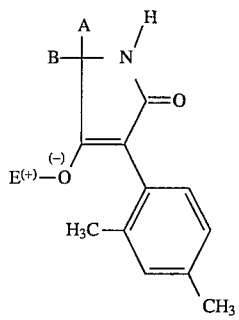

I-f

| A | B | E· |
|---|---|---|
| CH₃ | C₂H₅ | i-C₃H₇NH₃ |
| CH₃ | C₃H₇-n | i-C₃H₇NH₃ |
| CH₃ | C₃H₇-i | i-C₃H₇NH₃ |
| CH₃ | C₄H₉-n | i-C₃H₇NH₃ |
| CH₃ | C₄H₉-i | i-C₃H₇NH₃ |
| CH₃ | C₄H₉-s | i-C₃H₇NH₃ |
| CH₃ | C₄H₉-t | i-C₃H₇NH₃ |
| CH₃ | C₅H₁₁ | i-C₃H₇NH₃ |
| CH₃ | C₅H₁₁-i | i-C₃H₇NH₃ |
| C₂H₅ | C₂H₅ | i-C₃H₇NH₃ |
| CH₃ | C₃H₇ | i-C₃H₇NH₃ |
| C₃H₇-i | C₃H₇-i | i-C₃H₇NH₃ |
| —(CH₂)₂— | | i-C₃H₇NH₃ |
| —(CH₂)₄— | | i-C₃H₇NH₃ |
| —(CH₂)₅— | | i-C₃H₇NH₃ |
| —(CH₂)₆— | | i-C₃H₇NH₃ |
| —(CH₂)₇— | | i-C₃H₇NH₃ |
| CH₃ | C₂H₅ | Na |
| CH₃ | C₃H₇-n | Na |
| CH₃ | C₃H₇-i | Na |
| CH₃ | C₄H₉-n | Na |
| CH₃ | C₄H₉-i | Na |
| CH₃ | C₄H₉-s | Na |
| CH₃ | C₄H₉-t | Na |
| CH₃ | C₅H₁₁ | Na |
| CH₃ | C₅H₁₁-i | Na |
| C₂H₅ | C₂H₅ | Na |
| CH₃ | C₃H₇ | Na |
| C₃H₇-i | C₃H₇-i | Na |
| —(CH₂)₂— | | Na |
| —(CH₂)₄— | | Na |
| —(CH₂)₅— | | Na |
| —(CH₂)₆— | | Na |
| —(CH₂)₇— | | Na |

The following compounds of the formula (Ig) may be mentioned individually in addition to the compounds mentioned in the preparation examples:

TABLE 7

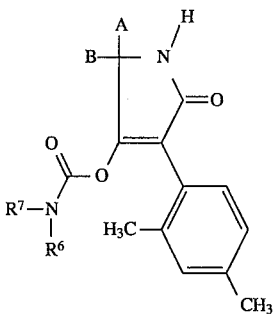

I-g

| A | B | R⁶ | R⁷ |
|---|---|---|---|
| CH₃ | C₂H₅ | CH₃ | CH₃ |
| CH₃ | C₃H₇-n | CH₃ | CH₃ |

TABLE 7-continued

I-g

| A | B | R⁶ | R⁷ |
|---|---|---|---|
| CH₃ | C₃H₇-i | CH₃ | CH₃ |
| CH₃ | C₄H₉-n | CH₃ | CH₃ |
| CH₃ | C₄H₉-i | CH₃ | CH₃ |
| CH₃ | C₄H₉-s | CH₃ | CH₃ |
| CH₃ | C₄H₉-t | CH₃ | CH₃ |
| CH₃ | C₅H₁₁ | CH₃ | CH₃ |
| CH₃ | C₅H₁₁-i | CH₃ | CH₃ |
| C₂H₅ | C₂H₅ | CH₃ | CH₃ |
| CH₃ | C₃H₇ | CH₃ | CH₃ |
| C₃H₇-i | C₃H₇-i | CH₃ | CH₃ |
| —(CH₂)₂— | | CH₃ | CH₃ |
| —(CH₂)₄— | | CH₃ | CH₃ |
| —(CH₂)₅— | | CH₃ | CH₃ |
| —(CH₂)₆— | | CH₃ | CH₃ |
| —(CH₂)₇— | | CH₃ | CH₃ |
| CH₃ | C₂H₅ | —(CH₂)₂—O—(CH₂)₂— | |
| CH₃ | C₃H₇-n | —(CH₂)₂—O—(CH₂)₂— | |
| CH₃ | C₃H₇-i | —(CH₂)₂—O—(CH₂)₂— | |
| CH₃ | C₄H₉-n | —(CH₂)₂—O—(CH₂)₂— | |
| CH₃ | C₄H₉-i | —(CH₂)₂—O—(CH₂)₂— | |
| CH₃ | C₄H₉-s | —(CH₂)₂—O—(CH₂)₂— | |
| CH₃ | C₄H₉-t | —(CH₂)₂—O—(CH₂)₂— | |
| CH₃ | C₅H₁₁ | —(CH₂)₂—O—(CH₂)₂— | |
| CH₃ | C₅H₁₁-i | —(CH₂)₂—O—(CH₂)₂— | |
| C₂H₅ | C₂H₅ | —(CH₂)₂—O—(CH₂)₂— | |
| CH₃ | C₃H₇ | —(CH₂)₂—O—(CH₂)₂— | |
| C₃H₇-i | C₃H₇-i | —(CH₂)₂—O—(CH₂)₂— | |
| —(CH₂)₂— | | —(CH₂)₂—O—(CH₂)₂— | |
| —(CH₂)₄— | | —(CH₂)₂—O—(CH₂)₂— | |
| —(CH₂)₅— | | —(CH₂)₂—O—(CH₂)₂— | |
| —(CH₂)₆— | | —(CH₂)₂—O—(CH₂)₂— | |
| —(CH₂)₇— | | —(CH₂)₂—O—(CH₂)₂— | |

In addition to the intermediates mentioned in the preparation examples, the following compounds of the formula (II) may be mentioned by way of example but not by way of limitation:

Methyl N-(2,4-dimethylphenylacetyl)-2-amino-2-methylbutyrate,
Methyl N-(2,4-dimethylphenylacetyl)-2-amino-2-methylvalerate;
Methyl N-(2,4-dimethylphenylacetyl)-2-amino-2-methylisovalerate,
Methyl N-(2,4-dimethylphenylacetyl)-2-amino-2-methylcaproate,
Methyl N-(2,4-dimethylphenylacetyl)-2-amino-2-methylisocaprate,
Methyl N-(2,4-dimethylphenylacetyl)-2-amino-2,3-dimethylvalerate,
Methyl N-(2,4-dimethylphenylacetyl)-2-amino-2-ethylbutyrate,
Methyl N-(2,4-dimethylphenylacetyl)-1-amino-cyclopentanoate
Methyl N-(2,4-dimethylphenylacetyl)-1-amino-cyclohexanoate
Methyl N-(2,4-dimethylphenylacetyl)-1-amino-cycloheptanoate, Methyl N-(2,4-dimethylphenylacetyl)-1-amino-cyclooctanoate,
Ethyl N-(2,4-dimethylphenyl acetyl)-2-amino-2-methylbutyrate,
Ethyl N-(2,4-dimethylphenylacetyl)-2-amino-2-methylvalerate;
Ethyl N-(2,4-dimethylphenylacetyl)-2-amino-2-methylisovalerate,
Ethyl N-(2,4-dimethylphenylacetyl)-2-amino-2-methylcaproate,
Ethyl N-(2,4-dimethylphenylacetyl)-2-amino-2-methylisocaproate,
Ethyl N-(2,4-dimethylphenylacetyl)-2-amino-2,3-dimethylvalerate,
Ethyl N-(2,4-dimethylphenylacetyl)-2-amino-2-ethylbutyrate,
Ethyl N-(2,4-dimethylphenylacetyl)-1-amino-cyclopentanoate
Ethyl N-(2,4-dimethylphenylacetyl)-1-amino-cyclohexanoate
Ethyl N-(2,4-dimethylphenylacetyl)-1-amino-cycloheptanoate,
Ethyl N-(2,4-dimethylphenylacetyl)-1-amino-cyclooctanoate, In addition to the intermediates mentioned in the preparation examples, the following compounds of the formula (XVI) may be mentioned by way of example but not by limitation:

N-(2,4-dimethylphenylacetyl)-2-amino-2-methyl-butyronitrile,
N-(2,4-dimethylphenylacetyl)-2-amino-2-methyl-valeronitrile,
N-(2,4-dimethylphenylacetyl)-2-amino-2-methyl-isovaleronitrile,
N-(2,4-dimethylphenylacetyl)-2-amino-2-methyl-capronitrile;
N-(2,4-dimethylphenylacetyl)-2-amino-2-methyl-isocapronitrile,
N-(2,4-dimethylphenylacetyl)-2-amino-2,3-dimethyl-valeronitrile,
N-(2,4-dimethylphenylacetyl)-2-amino-2-ethyl-butyronitrile,
N-(2,4-dimethylphenylacetyl)-1-amino-cyclopentanonitrile,
N-(2,4-dimethylphenylacetyl)-1-amino-cyclohexanonitrile,
N-(2,4-dimethylphenylacetyl)-1-amino-cycloheptanonitrile,
N-(2,4-dimethylphenylacetyl)-1-amino-cyclooctanonitrile, The acid halides of the formula (III), carboxylic anhydrides of the formula (IV), chloroformic esters or chloroformic thioesters of the formula (V), chloromonothioformic esters or chlorodithioformic esters of the formula (VI), alkyl halides of the formula (VII), sulphonyl chlorides of the formula (VIII), phosphorus compounds of the formula (IX) and metal hydroxides or amines of the formula (X) and (XI) and isocyanates or carbamoyl chlorides of the formula (XIII), all of which are furthermore required as starting substances for carrying out processes (B), (C), (D), (E), (F), (G) and (H) according to the invention, are generally known compounds of organic or inorganic chemistry.

Process (A) is characterized in that compounds of the formula (II), in which A, B and $R^8$ have the above-mentioned meaning, are subjected to intramolecular condensation reaction in the presence of bases.

Diluents which can be employed in process (A) according to the invention are all inert organic solvents. The following can preferably be used: hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, iso-butanol and tert-butanol.

Bases (deprotonating agents) which can be employed when carrying out process (A) according to the invention are all customary proton acceptors. The following can preferably be used: alkali metal oxides, alkali metal hydroxides, alkali metal carbonates, alkaline earth metal oxides, alkaline earth metal hydroxides and alkaline earth metal carbonates, such as sodium hydroxide, potassium hydroxide, magnesium oxide, calcium oxide, sodium carbonate, potassium carbonate and calcium carbonate, all of which can also be employed in the presence of phase transfer catalysts, such as, for example, triethylbenzylammonium chloride, tetrabutylammonium bromide, Adogen 464 or TDA 1*). In addition, alkali metals such as sodium or potassium can be employed. Other substances which can be employed are alkali metal amides, alkali metal hydrides, alkaline earth metal amides and alkaline earth metal hydrides, such as sodium amide, sodium hydride and calcium hydride, moreover alkali metal alcoholates, such as sodium methylate, sodium ethylate and potassium tert.-butylate.

*) Adogen 464=methyltrialkyl ($C_8$-$C_{10}$)ammonium chloride TDA 1=tris-(methoxyethoxyethyl)-amine When carrying out process (A) according to the invention, the reaction temperatures can be varied within a substantial range. In general, the process is carried out at temperatures between 0° C. and 250° C., preferably between 50° C. and 150° C.

In general, process (A) according to the invention is carried out under atmospheric pressure.

When carrying out process (A) according to the invention, the reactants of the formulae (II) and the deprotonating bases are generally employed in twice the equimolar amounts. However, it is also possible to use one or the other reactant in a larger excess (up to 3 mol).

Process (Bα) is characterized in that compounds of the formula (Ia) are reacted with carboxylic acid halides of the formula (III).

If the acid halides are used in process (Bα) according to the invention, then diluents which can be employed are all solvents which are inert towards these compounds. The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, in addition carboxylic esters, such as ethyl acetate, and also strongly polar solvents, such as dimethyl sulphoxide and sulpholane. If the acid halide is sufficiently stable to hydrolysis, the reaction can also be carried out in the presence of water.

If the corresponding carboxylic acid halides are used, then acid-binding agents which are suitable for the reaction in accordance with process (Bα) according to the invention are all customary acid acceptors. The following can preferably be used: tertiary amines, such as triethylamine, pyridine, diazabicyclooctane (DABCO), diazabicycloundecene (DBU), diazabicyclononene (DBN), Hünig base and N,N-dimethyl-aniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

When carrying out process (Bα) according to the invention, the reaction temperatures can also be varied within a substantial range, which also applies if carboxylic acid halides are used. In general, the process is carried out at temperatures between −20° C. and +150° C., preferably between 0° C. and 100° C.

When carrying out process (Bα) according to the invention, the starting substances of the formula (Ia) and the carboxylic acid halide of the formula (III) are generally used in approximately equivalent amounts. However, it is also possible to employ the carboxylic acid halide in a larger excess (up to 5 mol). Working-up is carried out by customary methods.

Process (Bβ) is characterized in that compounds of the formula (Ia) are reacted with carboxylic anhydrides of the formula (IV).

If, in process (Bβ) according to the invention, carboxylic anhydrides are used as reactants of the formula (IV), then diluents which can preferably be used are those which are also preferably suitable when acid halides are used. Besides, a carboxylic anhydride employed in excess can also simultaneously act as the diluent.

When carrying out process (Bβ) according to the invention, the reaction temperatures can be varied within a substantial range, which also applies if carboxylic anhydrides are used. In general, the process is carried out at temperatures between −20° C. and +150° C., preferably between 0° C. and 100° C.

When carrying out the process according to the invention, the starting substances of the formula (Ia) and the carboxylic anhydride of the formula (IV) are generally used in approximately equivalent amounts. However, it is also possible to employ the carboxylic anhydride in a larger excess (up to 5 mol). Working-up is carried out by customary methods.

In general, a procedure is followed in which diluent and excess carboxylic anhydride as well as the carboxylic acid which forms are removed by distillation or by washing with an organic solvent or with water.

Process (C) is characterized in that compounds of the formula (Ia) are reacted with chloroformic esters or chloroformic thioesters of the formula (V).

If the corresponding chloroformic esters or chloroformic thioesters are used, then acid-binding agents in the reaction in accordance with process (C) according to the invention are all customary acid acceptors. The following can preferably be used: tertiary amines, such as triethylamine, pyridine, DABCO, DBU, DBA, Hünig base and N,N-dimethylaniline, furthermore alkaline earth metal oxides, such as magnesium oxide and calcium oxide, furthermore alkali metal carbonates and alkaline earth metal carbonates, such as sodium carbonate, potassium carbonate and calcium carbonate, and also alkali metal hydroxides, such as sodium hydroxide and potassium hydroxide.

If the chloroformic esters or chloroformic thioesters are used, then diluents which can be employed in process (C) according to the invention are all solvents which are inert towards these compounds. The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, furthermore ketones, such as acetone and methyl isopropyl ketone, moreover ethers, such as diethyl ether, tetrahydrofuran and dioxane, in addition carboxylic esters, such as ethyl acetate, and also strongly polar solvents, such as dimethyl sulphoxide and sulpholane.

If the chloroformic esters or chloroformic thioesters are used as carboxylic acid derivatives of the formula (V), then the reaction temperatures can be varied within a substantial range when carrying out process (C) according to the invention. If the process is carried out in the presence of a diluent and of an acid-binding agent, then the reaction temperatures are generally between −20° C. and 100° C., preferably between 0° C. and 50° C.

Process (C) according to the invention is generally carried out under atmospheric pressure.

When carrying out process (C) according to the invention, the starting substances of the formula (Ia) and the chloroformic ester or chloroformic thioester of the formula (V) in question are generally used in approximately equivalent amounts. However, it is also possible to employ one or the other reactant in a larger excess (up to 2 mol). Working-up is then carried out by customary methods. In general, a procedure is followed in which precipitated salts are removed and the reaction mixture which remains is concentrated by stripping off the diluent.

In preparation process (D), approximately 1 mol of chloromonothioformic ester or chlorodithioformic ester of the formula (VI) is reacted at 0° to 120° C., preferably at 20° to 60° C., per mole of starting compound of the formula (Ia).

Suitable diluents which may be added are all inert polar organic solvents, such as ethers, amides sulphones or sulphoxides.

Dimethyl sulphoxide, tetrahydrofuran, dimethylformamide and dimethyl sulphide are preferably employed.

If, in a preferred embodiment, the enolate salt of the compound Ia is synthesized by adding strong deprotonating agents, such as, for example, sodium hydride or potassium tertiary butylate, a further addition of acid-binding agents can be dispensed with.

If acid-binding agents are employed, then suitable substances are customary inorganic or organic bases, sodium hydroxide, sodium carbonate, potassium carbonate, pyridine and triethylamine being mentioned by way of example.

The reaction can be carried out under atmospheric pressure or under increased pressure; it is preferably carried out under atmospheric pressure. Working-up is carried out by customary methods.

In preparation process (D$_\beta$), the equimolar amount, or an excess, of carbon disulphide is added per mole of starting compound of the formula (Ia). This process is preferably carried out at temperatures from 0° to 50° C. and, in particular, at 20° to 30° C.

Frequently, it is expedient to first prepare the corresponding salt from the compound of the formula (Ia) by adding a deprotonating agent (such as, for example, potassium tertiary butylate or sodium hydride). The compound (Ia) is reacted with carbon disulphide until the formation of the intermediate is complete, for example after stirring for several hours at room temperature.

The further reaction with the alkyl halide of the formula (VII) is preferably carried out at 0° to 70° C., in particular at 20° to 50° C. At least the equimolar amount of alkyl halide is employed.

The process is carried out under atmospheric pressure or under increased pressure, preferably under atmospheric pressure.

Again, working-up is carried out by customary methods.

In preparation process (E), approximately 1 mol of sulphonyl chloride (VIII) is reacted per mole of starting compound of the formula (Ia) at −20° to 150° C., preferably at 0° to 70° C.

Suitable diluents which may be added are all inert polar organic solvents, such as ethers, amides, nitriles, sulphones, sulphoxides or halogenated hydrocarbons, such as methylene chloride.

Dimethyl sulphoxide, tetrahydrofuran, dimethylformamide, dimethyl sulphide and methylen chloride are preferably employed.

If, in a preferred embodiment, the enolate salt of the compound Ia is synthesized by adding strong deprotonating agents (such as, for example, sodium hydride or potassium tertiary butylate), a further addition of acid-binding agents can be dispensed with.

If acid-binding agents are employed, then suitable substances are customary inorganic or organic bases, sodium hydroxide, sodium carbonate, potassium carbonate, pyridine and triethylamine being mentioned by way of example.

The reaction can be carried out under atmospheric pressure or under increased pressure, it is preferably carried out under atmospheric pressure. Working-up is carried out by customary methods.

To obtain compounds of the structure (Ie) 1 to 2, preferably 1 to 1.3 mol of the phosphorus compound of the formula (IX) are rected in preparation process (F) per mole of the compound (Ia) at temperatures between −40° C. and 150° C., preferably between −10° and 110° C.

Suitable diluents which may be added are all inert, polar organic solvents, such as ethers, amides, nitriles, alcohols, sulphides, sulphones, sulphoxides and the like.

Acetonitrile, dimethyl sulphoxide, tetrahydrofuran, dimethylformamide or methylene chloride are preferably employed.

Suitable acid-binding agents which may be added are customary inorganic or organic bases, such as hydroxides or carbonates. Examples which my be mentioned are sodium hydroxide, sodium carbonate, potassium carbonate, pyridine and triethylamine.

The reaction can be carried out under atmospheric pressure or under increased pressure, it is preferably carried out under atmospheric pressure. Working-up is carried out by customary methods of organic Chemistry. The end products obtained are preferably purified by crystallization, chromatography or by so-called "incipient distillation", i.e. removal of the volatile components in vacuo.

Process (G) is characterized in that compounds of the formula (Ia) are reacted with metal hydroxides (X) or amines (XI).

Diluents which can be employed in the process according to the invention are, preferably, ethers, such as tetrahydrofuran, dioxane or diethyl ether, or else alcohols, such as methanol, ethanol, isopropanol, but also water. Process (G) according to the invention is generally carried out under atmospheric pressure. The reaction temperatures are generally between −20° C. and 100° C., preferably between 0° C. and 50° C.

In preparation process ($H_\alpha$), approximately 1 mol of isocyanate, or isothiocyanate, of the formula (XII) is reacted per mole of starting compound of the formula (Ia) at 0° to 100° C., preferably at 20° to 50° C.

Suitable diluents which may be added are all inert organic solvents, such as ethers, amides, nitriles, sulphones or sulphoxides.

If appropriate, catalysts may be added to accelerate the reaction. Catalysts which are very advantageously employed are organotin compounds, such as, for example, dibutyltin dilaurate. The process is preferably carried out under atmospheric pressure.

In preparation process ($H_\beta$), approximately 1 mol of carbamoyl chloride of the formula (XIII) is reacted per mole of starting compound of the formula (Ia) at 0° to 150° C., preferably at 20° to 70° C.

Suitable diluents which may be added are all inert polar organic solvents, such as ethers, amides, sulphones or sulphoxides.

Dimethyl sulphoxide, tetrahydrofuran, dimethylformamide or methylene chloride are preferably employed.

If, in a preferred embodiment, the enolate salt of the compound (Ia) is synthesized by adding strong deprotonating agents (such as, for example, sodium hydride or potassium tertiary butylate), the further addition of acid-binding agents can be dispensed with.

If acid-binding agents are employed, then suitable substances are customary inorganic or organic bases, sodium hydroxide, sodium carbonate, potassium carbonate, triethylamine or pyridine being mentioned by way of example.

The reaction can be carried out under atmospheric pressure or under increased pressure, it is preferably carried out under atmospheric pressure. Working-up carried out by customary methods.

The active compounds are suitable for combating animal pests, preferably arthropods and nematodes, in particular insects and arachnids, which occur in agriculture, in forests, in the protection of stored products and of materials, and in the hygiene sector. They are active against normally sensitive and resistant species and against all or individual development stages. The above-mentioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni,*

*Saissetia oleae, Laodelphax striatellus, Nilaparvata lugens, Aonidiella aurantii, Aspidiotus hederae,* Pseudococcus spp. Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds according to the invention are not only active against plant, hygiene and stored product pests, but also, in the veterinary medicine sector, against animal parasites (ectoparasites and endoparasites), such as scaly ticks, Argasidae, scab mites, Trombidae, flies (stinging and sucking), parasitic fly larvae, lice, hair lice, bird lice, fleas and endoparasitic worms.

They are effective against normally sensitive and resistant types and strains and against all parasitic and non-parasitic developmental stages of the ectoparasites and endoparasites.

The active compounds according to the invention are distinguished by a powerful insecticidal and acaricidal activity.

They can be used particularly successfully for combating plant-damaging insects, such as, for example, against the larvae of the green rice leafhopper (*Nephotettix cincticips*), against the larvae of the mustard beetle (*Phaedon cochleariae*) or against the tobacco budworm (*Heliothis virescens*).

Moreover, they can be used in an outstanding manner for combating plant-damaging mites, such as, for example, against the greenhouse red spider mite (*Tetranychus urticae*) and against the fruit tree red spider mite (*Panonychus ulmi*).

The active compounds according to the invention can be also used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Arena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves; nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The active compounds according to the invention are highly suitable for selectively combating monocotyledon weeds in monocotyledon and dicotyledon cultures by the post-emergence method. For example, they can be employed very successfully in soya beans or winter wheat for controlling grass weeds.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, or example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural mineral, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dye-stuffs, and trace nutrients such as salts of iron, manganese, boron, copper, cobalt, molybdenum and zinc.

The formulations in general contain between 0.1 and 95% by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H, 3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beet, and 4-amino-6-(1,1-dimethylethyl)-3-methylthio-1,2,4-triazin-5(4H)-one (METRIBUZIN) for combating weeds in soya beans. Other suitable herbicides are 2,4-dichlorophenoxyacetic acid (2,4-D); 4-(2,4-dichlorophenoxy) butyric acid (2,4-DB); 2,4-dichlorophenoxypropionic acid (2,4-DP); 3-isopropyl-2,1,3-benzothiadiazin-4-one 2,2-dioxide (BEN-TAZONE); methyl 5-(2,4-dichlorophenoxy)-2-nitrobenzoate (BIFENOX); 3,5-dibromo-4-hydroxy-benzonitrile (BROMOXYNIL); 2-chloro-N-{[(4-methoxy-6-methyl-1,3,5-triazin-2-yl)-amino]-carbonyl}-benzenesulphonamide (CHLORSULFURON); 2-[4-(2,4-dichlorophenoxy)-phenoxy]-propionic acid, its methyl or its ethyl ester (DICLOFOPMETHYL); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid, its methyl or its ethyl ester (FENOXAPROP); [(4-amino-3,5-dichloro-6-fluoro-2-pyridinyl)-oxy]-acetic acid or its 1-methylheptyl ester (FLUROXYPYR); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)urea (ISOPROTURON); (2-methyl-4-chlorophenoxy)acetic acid (MCPA); (4-chloro-2-methylphenoxy)-propionic acid (MCPP); N-methyl-2-(1,3-benzothiazol-2-yloxy)acetanilide (MEFENACET); 2-{[[((4-methoxy-6-methyl-1,3,5-triazin-2-yl)-amino)-carbonyl]-amino]-sulphonyl}-benzoic acid or its (METSULFURON); N-(1-ethylpropyl)-3,4-dimethyl-2,6-dinitroaniline (PENDIMETHALIN); φ-(6-chloro-3-phenylpyridazin-4-yl)-S-octyl thiocarbonate (PYRIDATE); 4-ethylamino-2-t-butylamino-6-methylthio-s-triazine (TERBUTRYNE); and 3-[[[[(4-methoxy-6-methyl-1,3,5-triazin-2-yl)-amino]-carbonyl]-amino]-sulphonyl]-thiophene-2-carboxylate (THIAMETURON). Surprisingly, some mixtures also show synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example (Ia-1):

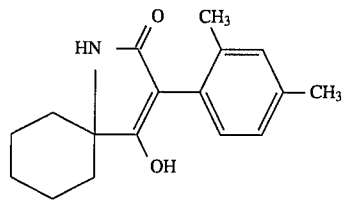

67.6 g (0.223 mol) of methyl N-(2,4-dimethylphenylacetyl)-1-amino-cyclohexanecarboxylate, dissolved in 450 ml of absolute toluene, are added dropwise to a suspension of 13.38 g (0.446 mol) of sodium hydride in 220 ml of absolute toluene, at boiling heat. The batch is refluxed until starting material is no longer detectable by thin-layer chromatography. Then, ethanol is added dropwise with ice-bath cooling until the evolution of hydrogen has ceased. The solvent is evaporated in vacuo, the residue is taken up in ethanol, and the mixture is acidified with 4N hydrochloric acid at 0° C. to 20° C. The precipitate which has separated out is filtered off with suction and dried. The resulting crude product is recrystallized from chloroform/n-hexane (1:3).

60.4 g (100% of theory) of 3-(2,4-dimethylphenyl)-5,5-pentamethylene-pyrrolidine-2,4-dione of melting point m.p. 223° C. are obtained.

Example (Ia-2):

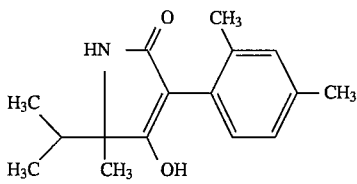

Analogously to Example (Ia-1), 3-(2,4-dimethylphenyl)-5-methyl-5-isopropyl-pyrrolidine-2,4-dione of melting point m.p. 115° C. is obtained.

Example (Ia-3):

Analogously to Example (Ia-1), 3-(2,4-dimethylphenyl)-5-methyl-5-sec-butyl-pyrrolidine-2,4 dione of melting point 125° C. is obtained.

Example (Ib-1)

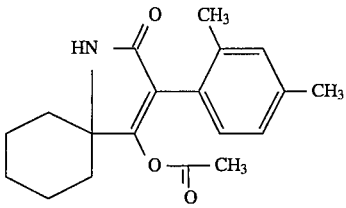

5.42 g (0.020 mol) of 3-(2,4-dimethylphenyl)-5,5-pentamethyl-pyrrolidine-2,4-dione are introduced into 70 ml of absolute dichloromethane, and the mixture is treated with 2.8 ml of triethylamine. 1.5 ml of acetyl chloride in 5 ml of absolute dichloromethane are added at 0°–10° C. and stirring of the batch is continued at room temperature. The end of the reaction is determined by thin-layer chromatography. The mixture is subsequently washed twice using in each case 200 ml of 0.5N sodium hydroxide solution, the organic phase is dried over magnesium sulphate and the solvent is stripped off in vacuo.

2.24 g (36% of theory) of 3-(2,4-dimethylphenyl)-5,5-pentamethylene-4-acetoxy-Δ3-pyrrolin-2-one of melting point m.p. 224° C. are obtained.

The end products of the formula (I-b) which are listed in Table 8 below are obtained analogously to Example (Ib-1) and following the general information given in the description of the processes according to the invention.

TABLE 8

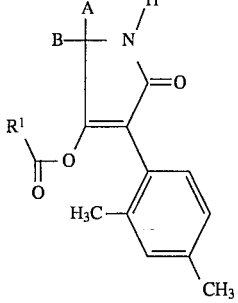

| Ex. No. | A | B | R¹ | Physical constant (°C.) |
|---|---|---|---|---|
| Ib-2 | CH₃ | i-C₃H₇ | CH₃ | m.p.: 176 |
| Ib-3 | CH₃ | i-C₃H₇ | i-C₃H₇ | m.p.: 154 |
| Ib-4 | CH₃ | i-C₃H₇ | t-C₄H₉ | m.p.: 151 |
| Ib-5 | —(CH₂)₅— | | i-C₃H₇ | m.p.: 191 |
| Ib-6 | —(CH₂)₅— | | t-C₄H₉ | m.p.: 193 |
| Ib-7 | CH₃ | i-C₃H₇ | C₂H₅ | m.p.: 118 |
| Ib-8 | CH₃ | i-C₃H₇ | C(CH₃)₂C₂H₅ | m.p.: 152 |
| Ib-9 | CH₃ | s-C₄H₉ | CH₃ | m.p.: 90 |
| Ib-10 | CH₃ | s-C₄H₉ | i-C₃H₇ | oil |
| Ib-11 | CH₃ | s-C₄H₉ | t-C₄H₉ | oil |

Example (Ic-1)

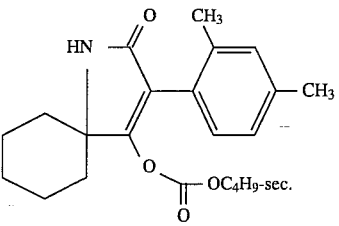

5.42 g (0.020 mol) of 3-(2,4-dimethylphenyl)-5,5-pentamethylene-pyrrolidine-2,4-dione are introduced into 70 ml of absolute dichloromethane, and the mixture is treated with 2.8 ml of triethylamine. 2.73 g of sec.-butyl chloroformate in 5 ml of absolute dichloromethane are added at 0°–10° C. and stirring of the batch is continued at room temperature. The end of the reaction is determined by thin-layer chromatography. The mixture is subsequently washed twice using in each case 200 ml of 0.5N sodium hydroxide solution, the organic phase is dried over magnesium sulphate and the solvent is stripped off in vacuo.

1.97 g (26% of theory) of O-(sec.-butyl) O-[3-(2,4-dimethylphenyl)]-5,5-pentamethylene-Δ3-pyrrolin-4-yl-2-one carbonate of melting point m.p. 169° C. are obtained.

The end products of the formula (Ic) listed in Table 9 below are obtained analogously to Example (Ic-1) and following the general information given in the description of the processes according to the invention

TABLE 9

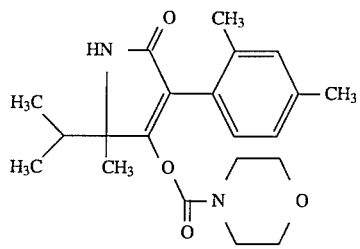

| Ex. No. | A | B | L | M | R² | Physical constant (°C.) |
|---|---|---|---|---|---|---|
| Ic-2 | CH₃ | i-C₃H₇ | O | O | C₂H₅ | m.p.: 149 |
| Ic-3 | CH₃ | i-C₃H₇ | O | O | s-C₄H₉ | m.p.: 132 |
| Ic-4 | —(CH₂)₅— | | O | O | C₂H₅ | m.p.: 181 |
| Ic-5 | CH₃ | i-C₃H₇ | O | S | i-C₃H₇ | m.p.: 152–153 |
| Ic-6 | CH₃ | i-C₃H₇ | O | O | CH₃ | m.p.: 152 |
| Ic-7 | CH₃ | i-C₃H₇ | O | O | i-C₃H₇ | oil |
| Ic-8 | CH₃ | i-C₃H₇ | O | O | i-C₄H₉ | m.p.: 36 |
| Ic-9 | CH₃ | s-C₄H₉ | O | O | C₂H₅ | m.p.: 60 |
| Ic-10 | CH₃ | s-C₄H₉ | O | O | s-C₄—H₉ | oil |

Example (Ie-1)

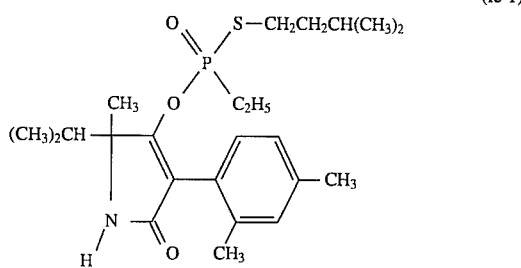
(Ie-1)

2 g (7.7 mmol) of 3-(2,4-dimethylphenyl)-5-isopropyl-5-methyl-pyrrolidine-2,4-dione are introduced into 20 ml of absolute tetrahydrofurane, and the mixture is treated with 1.2 ml of triethylamine. 2.3 g of ethyl-isopentylmercapto-thiophosphonic acid chloride are added at room temperature then the mixture is stirred at 50° C. for 24 hours. The reaction product is isolated by filtration over silica gel (eluent hexane/acetone 7/3) and evaporation of the solvent. 1.9 g (55.8% of theory) of the compound of formula (Ie-1) are obtained. Melting point: 98° C.

Example (Ie-2)

Analogously the compound of formula (Ie-2) of melting point 116° C. is obtained.

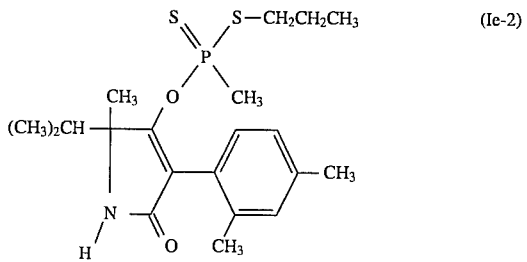
(Ie-2)

Example (Ig-1)

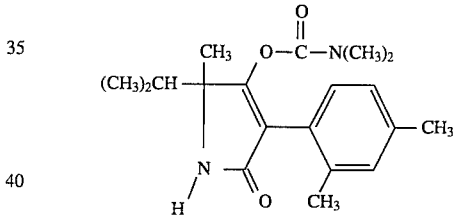

3.89 g (0.015 mol) of 3-(2,4-dimethylphenyl)-5-isopropyl-5-methyl-pyrrolidine-2,4-dione are introduced into 70 ml of absolute dichloromethane, and the mixture is treated with 2.1 ml (0.015 mol) of triethylamine. 1.76 ml (0.015 mol) of morpholinecarbamoyl chloride in 5 ml of absolute dichloromethane and 20 ml of 4-N,N-dimethylaminopyridine (Steglich base) are added at 0°–10° C. The reaction mixture is refluxed and the end of the reaction is determined by thin-layer chromatography. The mixture is washed twice using 100 ml of 0.5N sodium hydroxide solution, the organic phase is dried over magnesium sulphate and the solvent is stripped off in vacuo.

After recrystallization from methyl tert.-buthyl ether/n-hexane, 4.4 g (79% of theory) of 4-morpholinecarbamoyl-[3-(2,4-dimethylphenyl)-5-isopropyl-5-methyl-Δ3-pyrrolin-2-one of melting point m.p. 152°–153° C. are obtained.

Example (Ig-2)

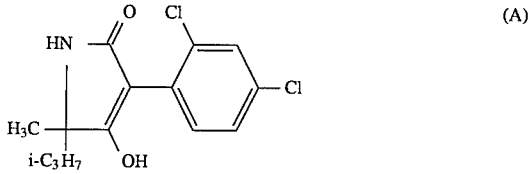

Analogously to Example (Ig-1) 4-dimethylcarbamoyl-[3-(2,4-dimethylphenyl)]-5-isopropyl-5-methyl-Δ3-pyrrolin-2-one of melting point m.p. 220° C. is obtained. below were employed as comparison substances:

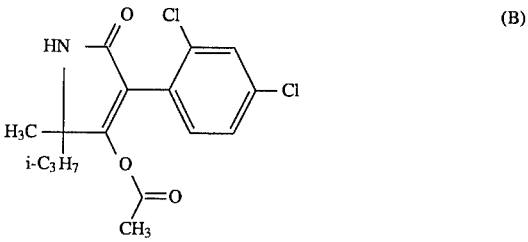
(A)

3-(2,4-Dichlorophenyl)-5-methyl-5-isopropyl-pyrrolidine-2,4-dione, disclosed in EP 456,063

(B)

3-(2,4-Dichlorophenyl)-5-methyl-5-isopropyl-4-acetoxy-
Δ3-pyrrolin-2-one, disclosed in EP 456,063

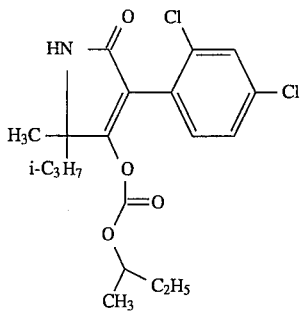
(C)

O-(sec.-butyl)-O-[3-(2,4-dichlorophenyl)]-5-methyl-5-iso-
propyl-Δ3-pyrrolin-4-yl-2-one carbonate, disclosed in EP
456,063

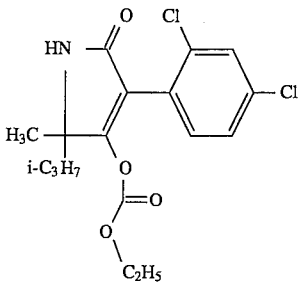
(D)

O-(ethyl)-O-[3-(2,4-dichlorophenyl)]-5-methyl-5-isopro-
pyl-Δ3-pyrrolin-4-yl-2-one carbonate, disclosed in EP
456,063

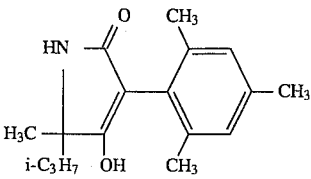
(E)

3-(2,4,6-Trimethylphenyl)-5-methyl-5-isopropyl-pyrroli-
dine-2,4-dione, disclosed in EP 456,063

Example A

Post-emergence test

| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, a clearly superior activity and crop plant selectivity compared with the prior art is shown, for example, by the compounds of Preparation Example (Ia-2), (Ib-2), (Ib-3), (Ic-2) and (Ic-3).

In this test the following results were obtained at an exemplary application rate of 125 g/ha, the active compounds being tolerated well to very well by soja beans:

| Plant | % Activity | Compound of Example No. | Preparation |
|---|---|---|---|
| Digitaria | >70 | Ia-2, Ib-2, Ib-3, Ic-2, Ic-3 | |
| Cynodon | >40 | Ia-2, Ib-2, Ib-3, Ic-2, Ic-3 | |
| Setaria | 90 | Ia-2, Ib-2, Ib-3, Ic-2, Ic-3 | |

Example B

Phaedon larvae test

| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), while the leaves are still moist.

After the specified periods of time, the plants are infested with mustard beetle larvae (*Phaedon cochleariae*). After intervals of 7 days, the destruction in % is determined. 100% means that all the beetle larvae have been killed; 0% means that none of the beetle larvae have been killed.

In this test, a destruction of 100% after 7 days is shown, for example, by the compounds of Preparation Examples (Ib-3) and (Ic-2) at an exemplary active compound concentration of 0.01%.

Example C

*Heliothis virescens* test

| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated mount of solvent and the stated amount of emulsifier, and the concentrate is diluted with water to the desired concentration.

Soya bean shoots (*Glycine max*) are treated by being dipped into the preparation of the active compound of the desired concentration and are infested with tobacco budworm caterpillars (*Heliothis virescens*) while the leaves are still moist.

After the specified periods of time, the destruction in is determined. 100% means that all animals have been killed; 0% means that none of the caterpillars have been killed.

In this test, a destruction of 100% after 7 days is shown, for example, by the compounds of the Preparation Examples (Ib-5), (Ic-1), (Ic-3) and (Ic-4) at an exemplary active compound concentration of 0.1%.

Example D

Nephotettix test

| Solvent: | 7 parts by weight of dimethylformamide |
| --- | --- |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Rice seedlings (*Oryzae sativa*) are treated by being dipped into the preparation of the active compound of the desired concentration and are infested with larvae of the green rice leafhopper (*Nephotettix cincticeps*) while the leaves are still moist.

After the specified periods of time, the destruction in % is determined. 100% means that all leafhoppers have been killed; 0% means that none of the leafhoppers have been killed.

In this test, a destruction of 100% after 7 days is shown, for example, by the compound of the Preparation Example (Ib-3) at an exemplary active compound concentration of 0.01%.

Example E

Tetranychus test (OP resistant)

| Solvent: | 3 parts by weight of dimethylformamide |
| --- | --- |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with all development stages of the greenhouse red spider mite or two-spotted spider mite (*Tetranychus urticae*) are treated by being dipped into the preparation of active compound of the desired concentration.

After the specified periods of time, the destruction in % is determined. 100% means that all spider mites have been killed; 0% means that none of the spider mites have been killed.

In this test, a destruction of 100% after 14 days is shown, for example, by the compounds of the Preparation Examples (Ib-5), (Ic-1), (Ic-2), (Ic-3) and (Ic-4) at an exemplary active compound concentration of 0.02%.

Example F

Panonychus test

| Solvent: | 3 parts by weight of dimethylformamide |
| --- | --- |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Young plant trees (*Prunus domestica*) which have an approximate height of 30 cm and which are heavily infested with all development stages of the fruit tree red spider mite (*Panonychus ulmi*) are treated by being dipped into the preparation of active compound of the desired concentration.

After the specified periods of time, the destruction in is determined. 100% means that all spider mites have been killed; 0% means that none of the spider mites have been killed.

In this test, a destruction of 100% after 14 days is shown, for example, by the compounds of the Preparation Examples (Ib-3), (Ic-2) and (Ic-3) at an exemplary active compound concentration of 0.02%.

We claim:

1. A dialkyl-1-H-3-(2,4-dimethylphenyl)-pyrrolidine-2,4-dione of the formula

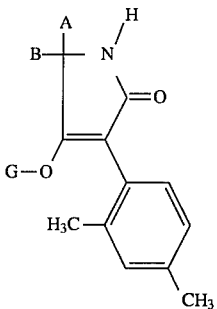

in which

A represents alkyl which is optionally substituted by halogen and

B represents $C_2$–$C_{10}$-alkyl or

A and B together with the carbon atom to which they are bonded represent an unsubstituted spiro carbocyclic ring, G represents hydrogen.

2. A pesticidal or herbicidal composition which comprises an effective amount of a compound according to claim 1 and diluent.

3. A method for combatting pests or undesired plant overgrowth, which comprises applying an effective amount of a compound according to claim 1, to a said pest or plant or to their environment.

4. A compound according to claim 1, wherein such compound is

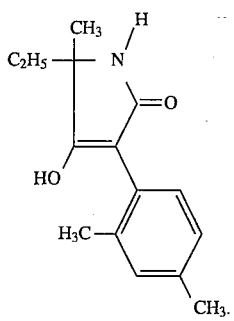
5. A compound according to claim 1, wherein such compound is
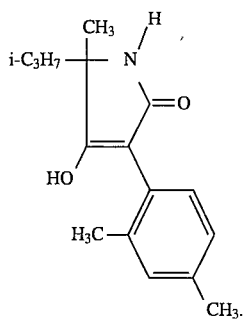
6. A compound according to claim 1, wherein such compound is
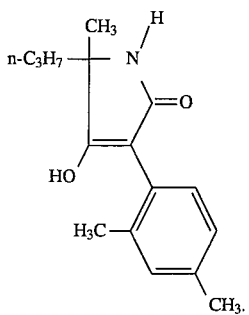
7. The method according to claim 3, wherein such compound is
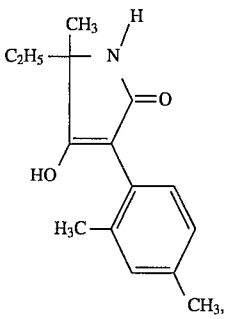
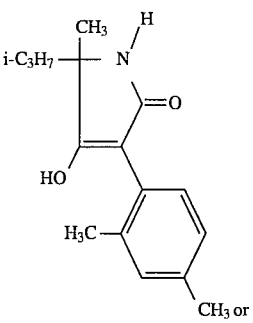
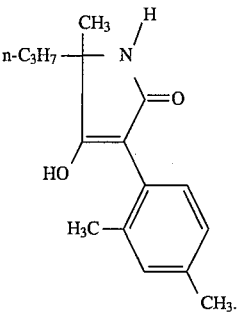
* * * * *